(12) United States Patent
Raheja et al.

(10) Patent No.: US 11,306,399 B2
(45) Date of Patent: Apr. 19, 2022

(54) NANOPARTICLE COMPOSITIONS

(71) Applicant: JANUARY THERAPEUTICS, INC., San Diego, CA (US)

(72) Inventors: Raj Raheja, San Diego, CA (US); Robin M. Jackman, San Diego, CA (US); Jason A. Kahana, San Diego, CA (US)

(73) Assignee: JANUARY THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 16/992,036

(22) Filed: Aug. 12, 2020

(65) Prior Publication Data

US 2021/0047358 A1 Feb. 18, 2021

Related U.S. Application Data

(60) Provisional application No. 62/886,255, filed on Aug. 13, 2019.

(51) Int. Cl.
| | |
|---|---|
| *A61K 9/19* | (2006.01) |
| *A61K 9/51* | (2006.01) |
| *A61P 35/00* | (2006.01) |
| *C07H 19/10* | (2006.01) |
| *C23F 1/18* | (2006.01) |
| *H01J 37/20* | (2006.01) |
| *C01B 32/194* | (2017.01) |
| *C23F 1/08* | (2006.01) |

(52) U.S. Cl.
CPC ............... *C23F 1/18* (2013.01); *A61K 9/19* (2013.01); *A61K 9/5169* (2013.01); *A61P 35/00* (2018.01); *C01B 32/194* (2017.08); *C07H 19/10* (2013.01); *C23F 1/08* (2013.01); *H01J 37/20* (2013.01); *C01B 2204/02* (2013.01); *C01B 2204/04* (2013.01); *H01J 2235/183* (2013.01); *H01J 2237/20* (2013.01); *H01J 2237/26* (2013.01)

(58) Field of Classification Search
CPC ........... C07H 19/10; A61P 35/00; A61K 9/19; A61K 9/5169
See application file for complete search history.

(56) References Cited

U.S. PATENT DOCUMENTS

| | | |
|---|---|---|
| 10,071,084 B2 | 9/2018 | Lee et al. |
| 2010/0160249 A1 | 6/2010 | Couvreur et al. |
| 2012/0328701 A1 | 12/2012 | Edelson et al. |
| 2013/0131008 A1 | 5/2013 | Cui et al. |
| 2014/0128339 A1 | 5/2014 | Girijavallabhan et al. |
| 2014/0199404 A1 | 7/2014 | Heise |
| 2015/0105341 A1 | 4/2015 | Beigelman et al. |
| 2018/0155385 A1 | 6/2018 | Dousson et al. |
| 2018/0289620 A1 | 10/2018 | Desai et al. |
| 2020/0369695 A1 | 11/2020 | Raheja et al. |
| 2021/0007999 A1 | 1/2021 | Raheja et al. |
| 2021/0038628 A1 | 2/2021 | Raheja et al. |

FOREIGN PATENT DOCUMENTS

| | | | |
|---|---|---|---|
| CN | 103239733 A | 8/2013 | |
| CN | 101732258 B | 12/2013 | |
| WO | WO-2007022073 A2 | 2/2007 | |
| WO | WO-2013096679 A1 * | 6/2013 | ........... C07H 19/207 |
| WO | WO-2014138278 A1 | 9/2014 | |
| WO | WO-2015134334 A1 | 9/2015 | |
| WO | WO-2016068341 A1 | 5/2016 | |
| WO | WO-2016188943 A1 | 12/2016 | |
| WO | WO-2017120537 A1 | 7/2017 | |
| WO | WO-2019027905 A1 | 2/2019 | |
| WO | WO-2019169323 A1 | 9/2019 | |
| WO | WO-2019169324 A1 | 9/2019 | |
| WO | WO-2020041050 A1 | 2/2020 | |
| WO | WO-2020041051 A1 | 2/2020 | |
| WO | WO-2020223530 A1 | 11/2020 | |
| WO | WO-2021030472 A1 | 2/2021 | |

OTHER PUBLICATIONS

Meier et al. Chapter 15, The cycloSal-Nucleotide Delivery System, pp. 353-401, Peters, Godefridus J., ed. Deoxynucleoside analogs in cancer therapy. Springer Science & Business Media, 2007 (Year: 2007).*

Madhumita Choudhuri and Alokmay Datta 2018 J. Phys.: Condens. Matter 30 355002 (Year: 2018).*

Park, Chulhun, et al. "The roles of short and long chain fatty acids on physicochemical properties and improved cancer targeting of albumin-based fattigation-platform nanoparticles containing doxorubicin." International journal of pharmaceutics 564 (Apr. 13, 2019): 124-135. (Year: 2019).*

Berge et al. Pharmaceutical Salts. Journal of Pharmaceutical Sciences 66(1):1-19 (Jan. 1977).

Bundgaard. Chapter 5: Design and Application of Prodrugs. A Textbook of Drug Design and Development, (pp. 113-191) (1991).

Bundgaard. Design of Prodrugs. Elsevier. Chapter 1. pp. 1-3 (1985).

Bundgaard. Means to Enhance Penetration: Prodrugs as a Means to Improve the Delivery of Peptide Drugs. Advanced Drug Delivery Review 8:1-38 (1992).

Lee et al. Synthesis and characterization of positive-charge functionalized mesoporous silica nanoparticles for oral drug delivery of an anti-inflammatory drug. Advanced Functional Materials 18:3283-3292 (2008).

Meng et al. Use of a lipid-coated mesoporous silica nanoparticle platform for synergistic gemcitabine and paclitaxel delivery to human pancreatic cancer in mice. ACS NANO 9(4):3540-3557 (2015).

PCT/US2018/044389 International Search Report and Written Opinion dated Nov. 29, 2018.

PCT/US2018/044389 Invitation to Pay Additional Fees dated Oct. 2, 2018.

(Continued)

*Primary Examiner* — Abigail Vanhorn

(74) *Attorney, Agent, or Firm* — Wilson Sonsini Goodrich & Rosati

(57) ABSTRACT

Provided herein are nanoparticle compositions comprising an organophosphate compound and pharmaceutically acceptable carriers.

18 Claims, 1 Drawing Sheet

(56) References Cited

OTHER PUBLICATIONS

PCT/US2019/020389 International Search Report and Written Opinion dated Jul. 9, 2019.
PCT/US2019/020389 Invitation to Pay Additional Fees dated May 2, 2019.
PCT/US2019/020391 International Search Report and Written Opinion dated May 14, 2019.
Widder et al. Section III: Prodrugs Kinetics. Method in Enzymology. 112:309-396 (1985).
Yu et al.: An in vitro and in vivo study of gemcitabine-loaded albumin nanoparticles in a pancreatic cancer cell line. Int J Nanomedicine. 10: 6825-6834 (2015).
Bundgard, H. Design of Prodrugs. 1985; pp. 7-9, 21-24 (Elsevier, Amsterdam).
PCT/US2020/045985 International Search Report and Written Opinion dated Nov. 24, 2020.
Golub et al., Molecular classification of cancer: class discovery and class prediction by gene expression monitoring. Science. 286(5439):531-537 (1999).
Lansakara et al. Synthesis and in vitro evaluation of novel lipophilic monophosphorylated gemcitabine derivatives and their nanoparticles. Int J Pharm 429(1-2):123-34 (2012).
U.S. Appl. No. 16/635,469 Office Action dated Jun. 2, 2021.
Sleep. Albumin and its application in drug delivery. Expert Opin Drug Deliv. 12(5):793-812 (2015).

\* cited by examiner

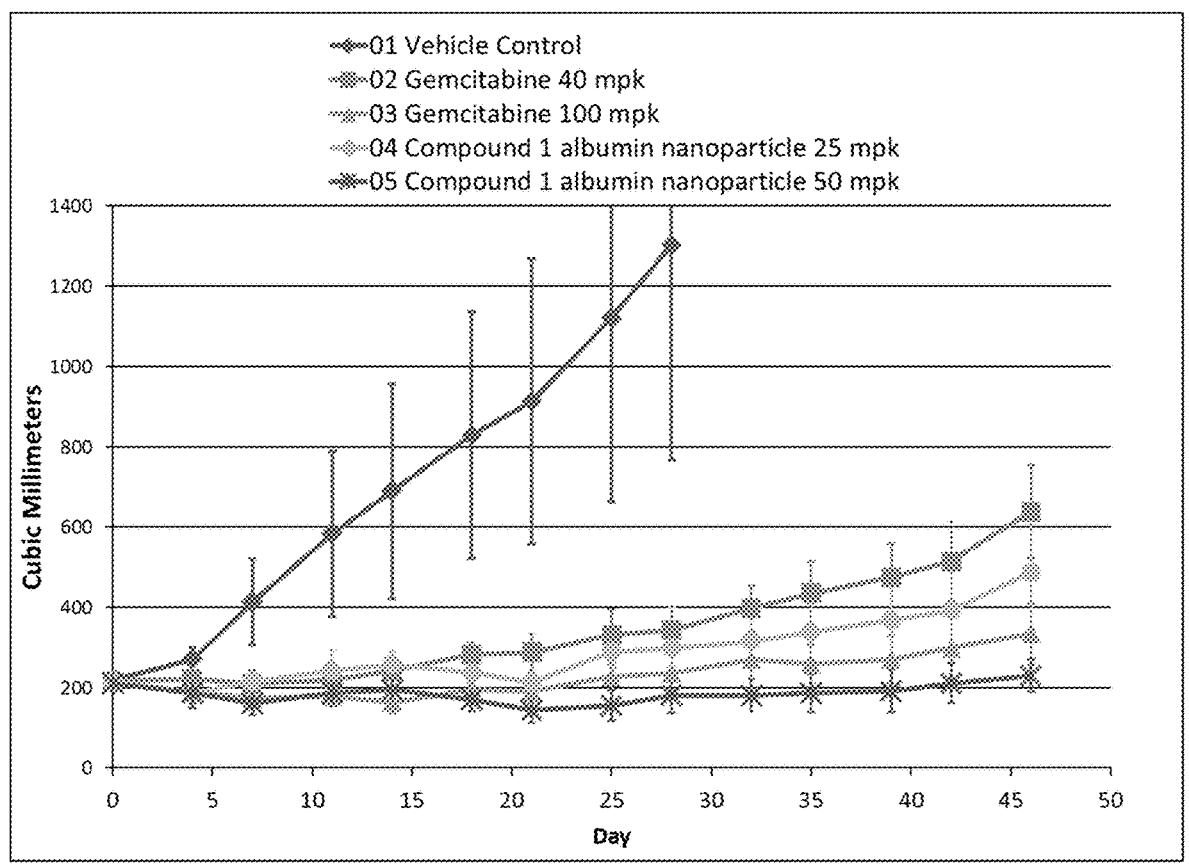

NANOPARTICLE COMPOSITIONS

CROSS-REFERENCE

This application claims benefit of U.S. Provisional Application No. 62/886,255, filed on Aug. 13, 2019, which is herein incorporated by reference in its entirety.

BACKGROUND

Nucleoside or nucleotide derivatives are widely used in treating cancer or viral infections.

BRIEF SUMMARY OF THE DISCLOSURE

This disclosure provides, for example, nanoparticle compositions comprising an organophosphate compound described herein, their use as medicinal agents, and processes for their preparation. The disclosure also provides for the use of the nanoparticle compositions described herein as medicaments and/or in the manufacture of medicaments for the treatment of a variety of diseases, including cancer and viral infections.

Provided in one aspect is a compound that is:

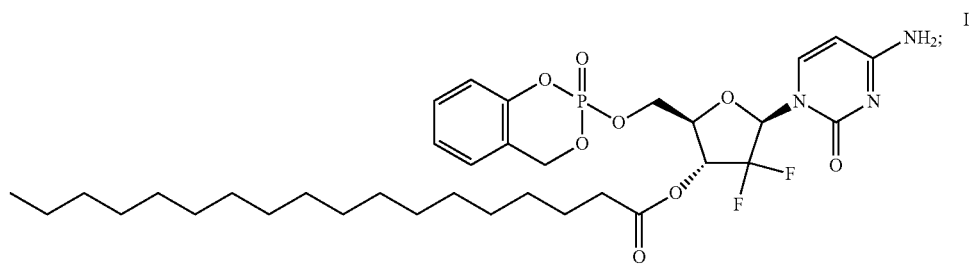 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

or a pharmaceutically acceptable salt thereof.

Provided in another aspect is a pharmaceutical composition comprising a compound, or a pharmaceutically acceptable salt thereof, that is:

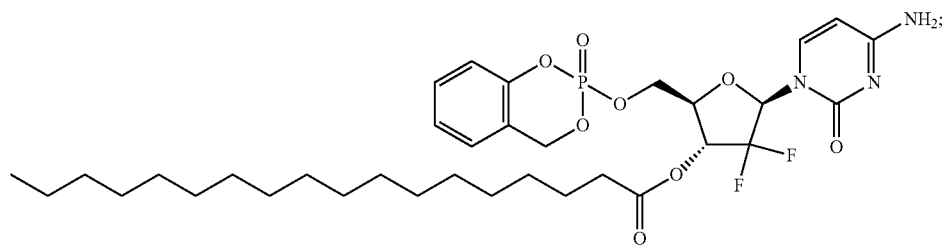 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

and at least one pharmaceutically acceptable excipient.

Provided in another aspect is a method of treating cancer in a patient in need thereof, comprising administering to the patient a therapeutically effective amount of a compound, or a pharmaceutically acceptable salt thereof, that is:

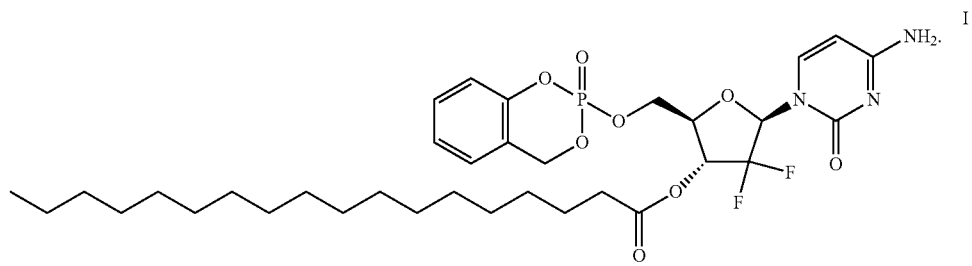 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

Provided in another aspect is a method of treating an infectious disease in a patient in need thereof, comprising administering to the patient a therapeutically effective amount of a compound, or a pharmaceutically acceptable salt thereof, that is:

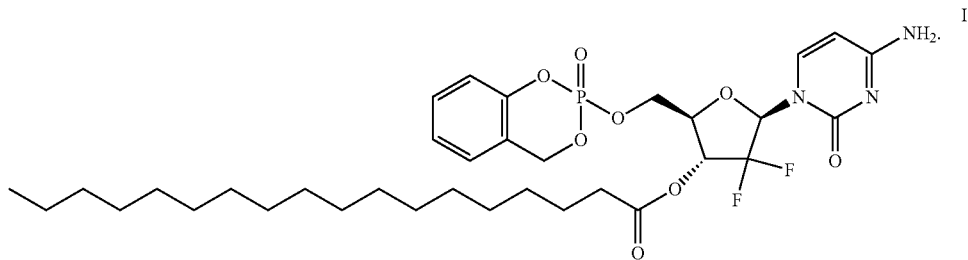 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

Provided in another aspect is a composition comprising nanoparticles, wherein the nanoparticles comprise a pharmaceutically acceptable carrier comprising albumin and a compound that is:

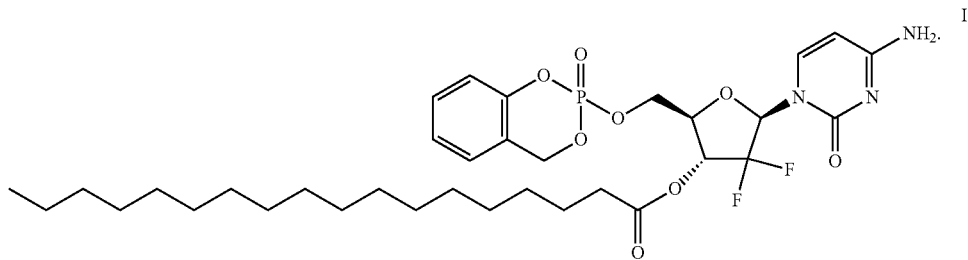 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

position. In some embodiments, the composition comprises from about 0.9% to about 24% by weight of the compound. In some embodiments, the composition comprises from about 1.8% to about 16% by weight of the compound. In some embodiments, the composition comprises from about 76% to about 99% by weight of the pharmaceutically acceptable carrier. In some embodiments, the composition comprises from about 84% to about 98% by weight of the pharmaceutically acceptable carrier.

In some embodiments, the nanoparticles have an average diameter of about 1000 nm or less for at least about 15 minutes after nanoparticle formation. In some embodiments, the nanoparticles have an average diameter of about 10 nm or greater for at least about 15 minutes after nanoparticle formation. In some embodiments, the nanoparticles have an average diameter of from about 10 nm to about 1000 nm for at least about 15 minutes after nanoparticle formation. In some embodiments, the nanoparticles have an average diameter of about 1000 nm or less for at least about 4 hours after nanoparticle formation. In some embodiments, the nanoparticles have an average diameter of about 10 nm or greater for at least about 4 hours nanoparticle formation. In some embodiments, the nanoparticles have an average diameter of from about 10 nm to about 1000 nm for at least about 4 hours after nanoparticle formation.

In some embodiments, the nanoparticles have an average diameter of from about 10 nm to about 1000 nm. In some embodiments, the nanoparticles have an average diameter of from about 30 nm to about 250 nm. In some embodiments, the albumin is human serum albumin. In some embodiments, the molar ratio of the compound to pharmaceutically acceptable carrier is from about 1:1 to about 20:1. In some embodiments, the molar ratio of the compound to pharmaceutically acceptable carrier is from about 2:1 to about 12:1. In some embodiments, the nanoparticles are suspended, dissolved, or emulsified in a liquid. In some embodiments, the composition is sterile filterable.

In some embodiments, the composition is dehydrated. In some embodiments, the composition is a lyophilized com- In some embodiments, the composition is reconstituted with an appropriate biocompatible liquid to provide a reconstituted composition. In some embodiments, the appropriate biocompatible liquid is a buffered solution. In some embodiments, the appropriate biocompatible liquid is a solution comprising dextrose. In some embodiments, the appropriate biocompatible liquid is a solution comprising one or more salts. In some embodiments, the appropriate biocompatible liquid is sterile water, saline, phosphate-buffered saline, 5% dextrose in water solution, Ringer's solution, or Ringer's lactate solution. In some embodiments, the nanoparticles have an average diameter of from about 10 nm to about 1000 nm after reconstitution. In some embodiments, the nanoparticles have an average diameter of from about 30 nm to about 250 nm after reconstitution.

In some embodiments, the composition is suitable for injection. In some embodiments, the composition is suitable for intravenous administration. In some embodiments, the composition is administered intraperitoneally, intraarterially, intrapulmonarily, orally, by inhalation, intravesicularly, intramuscularly, intratracheally, subcutaneously, intraocularly, intrathecally, intratumorally, or transdermally. In some embodiments, the compound is an anticancer agent. In some embodiments, the compound is an antiviral agent.

Provided in one aspect is a method of treating a disease in a subject in need thereof comprising administering any one of the compositions described herein. In some embodiments, the disease is cancer. In some embodiments, the disease is caused by an infection. In some embodiments, the infection is viral.

Provided in another aspect is a method of delivering a compound that is

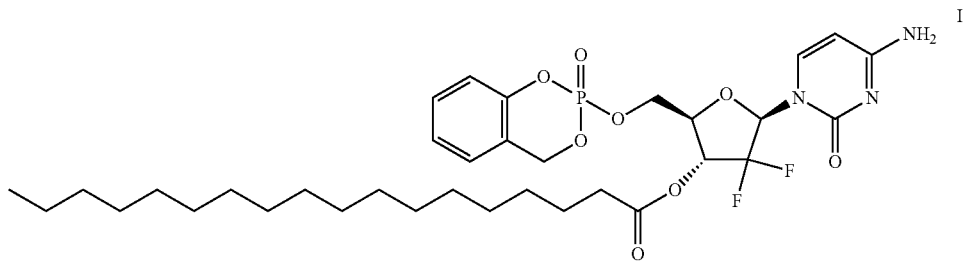

to a subject in need thereof comprising administering any one of the compositions described herein.

Provided in another aspect is a process of preparing any one of the composition described herein comprising a) dissolving a compound that is:

(Compound 1)

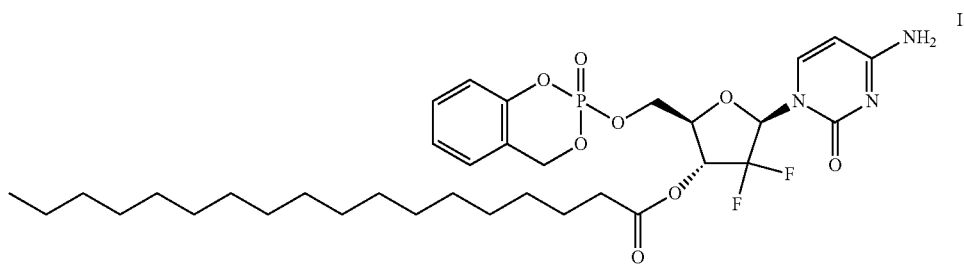 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

in a volatile solvent to form a solution comprising dissolved Compound 1;

b) adding the solution comprising the dissolved Compound 1 to a pharmaceutically acceptable carrier in an aqueous solution to form an emulsion;

c) subjecting the emulsion to homogenization to form a homogenized emulsion; and d) subjecting the homogenized emulsion to evaporation of the volatile solvent to form any one of the compositions described herein.

In some embodiments, the volatile solvent is a chlorinated solvent, alcohol, ketone, ester, ether, acetonitrile, or any combination thereof. In some embodiments, the volatile solvent is chloroform, ethanol, methanol, or butanol. In some embodiments, the homogenization is high pressure homogenization. In some embodiments, the emulsion is cycled through high pressure homogenization for an appropriate amount of cycles. In some embodiments, the appropriate amount of cycles is from about 2 to about 10 cycles. In some embodiments, the evaporation is accomplished with a rotary evaporator. In some embodiments, the evaporation is under reduced pressure.

BRIEF DESCRIPTION OF THE FIGURE

The Figure shows tumor growth inhibition in an in vivo xenograft efficacy model in human ovarian tumor-bearing mice treated with a nanoparticle formulation of Compound 1, gemcitabine, or vehicle control.

DETAILED DESCRIPTION OF THE DISCLOSURE

This application recognizes that the use of nanoparticles as a drug delivery platform is an attractive approach as nanoparticles provide the following advantages: more specific drug targeting and delivery, reduction in toxicity while maintaining therapeutic effects, greater safety and biocompatibility, and faster development of new safe medicines. The use of a pharmaceutically acceptable carrier, such as a protein, is also advantageous as proteins, such as albumin, are nontoxic, non-immunogenic, biocompatible, and biodegradable.

This application also recognizes that nucleoside or nucleotide derivatives are difficult to formulate into dosage forms that achieve and/or optimize the desired therapeutic effect(s) while minimizing its adverse effects. As such, there exists a need to develop compositions that deliver nucleoside or nucleotide derivatives with improved drug delivery and efficacy.

The application also recognizes that, in a non-limiting example, that chemically modifying a nucleoside or nucleotide into the corresponding prodrug form allows for the formulation of a nanoparticle composition wherein albumin is the carrier. In some instances, a wide variety of nucleosides or nucleotides is compatible for use, regardless of nitrogenous base (either natural or non-natural base), ring structure of the sugar moiety (either cyclic or acyclic), and number of phosphate groups (either none or containing at least one phosphate group). In one aspect provided herein, suitable nucleotide derivatives, such as Compound 1 described herein, are used to prepare nanoparticle formulations comprising albumin as a carrier.

Provided herein are compositions comprising nanoparticles that allow for the drug delivery of the nucleotide derivative Compound 1 described herein. These nanoparticle compositions further comprise pharmaceutically acceptable carriers that interact with the nucleoside derivative described herein to provide the compositions in a form that is suitable for administration to a subject in need thereof. In some embodiments, this application recognizes that Compound 1, which is a prodrug of gemcitabine, as described herein with specific pharmaceutically acceptable carriers, such as the albumin-based pharmaceutically acceptable carriers described herein, provide nanoparticle formulations that are stable. Also, this application recognizes that, in some instances, use of unmodified nucleoside or nucleotide (e.g. without forming the prodrug as described herein) with the albumin-based pharmaceutically acceptable carriers described herein do not result in stable nanoparticle formulations.

Nucleoside derivatives or analogs constitute a major class of chemotherapeutic agents and are used for the treatment of patients with cancer. This group of agents, known as antimetabolites, includes a variety of pyrimidine and purine nucleoside derivatives with cytotoxic activity in both hematological and solid tumors. Gemcitabine (2',2'-difluoro-2'-deoxycytidine) is a pyrimidine nucleoside analogue, shown to be active against several solid tumor types.

Both innate and acquired resistance to nucleoside analogues is a problem in the treatment of cancer and is regarded as a driver of poor patient survival outcomes. Gemcitabine faces inherent and acquired cancer resistance mechanisms that limit its effectiveness. These include (i) poor conversion of gemcitabine into the active forms, dFdCDP and dFdCTP; (ii) rapid degradation into inactive or toxic byproducts; and (iii) limited uptake by cancer cells. These effects are due to multiple factors including the following: (i) down-regulation of the key initial phosphorylating enzyme deoxycytidine kinase (dCK) required to convert gemcitabine into the monophosphate form; (ii) expression of the key deactivating enzyme cytidine deaminase; and (iii) deficiency of nucleoside transporter proteins. In addition, increased expression and/or activity of cytidine deaminase (CDA) increases the degradation of gemcitabine into the toxic metabolite 2',2'-difluoro-2'-deoxyuridine (dFdU). Similarly, increased expression of ribonucleoside-disphosphate reductase large subunit (RRM1) can lead to increased intracellular concentrations of endogenous nucleoside precursors, avoiding gemcitabine incorporation. Because of these and other processes, single agent gemcitabine has limited activity in cancer treatment.

Albumin nanoparticle delivery of encapsulated gemcitabine may allow efficacy in vivo at lower doses vs. unencapsulated gemcitabine. This more effective treatment with albumin nanoparticles may lead to a longer lasting treatment of tumors as compared to gemcitabine alone. In addition, lower dosing with equal or better efficacy, bypassing of potential resistance mechanisms, and/or albumin nanoparticle preferential targeting to tumors could each lead to potential reduced toxicities for a similar level of efficacy or greater efficacy not attainable with single agent gemcitabine.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

In some embodiments, the compound disclosed herein contains more than one asymmetric center and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

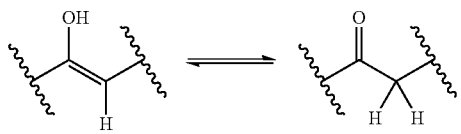

-continued

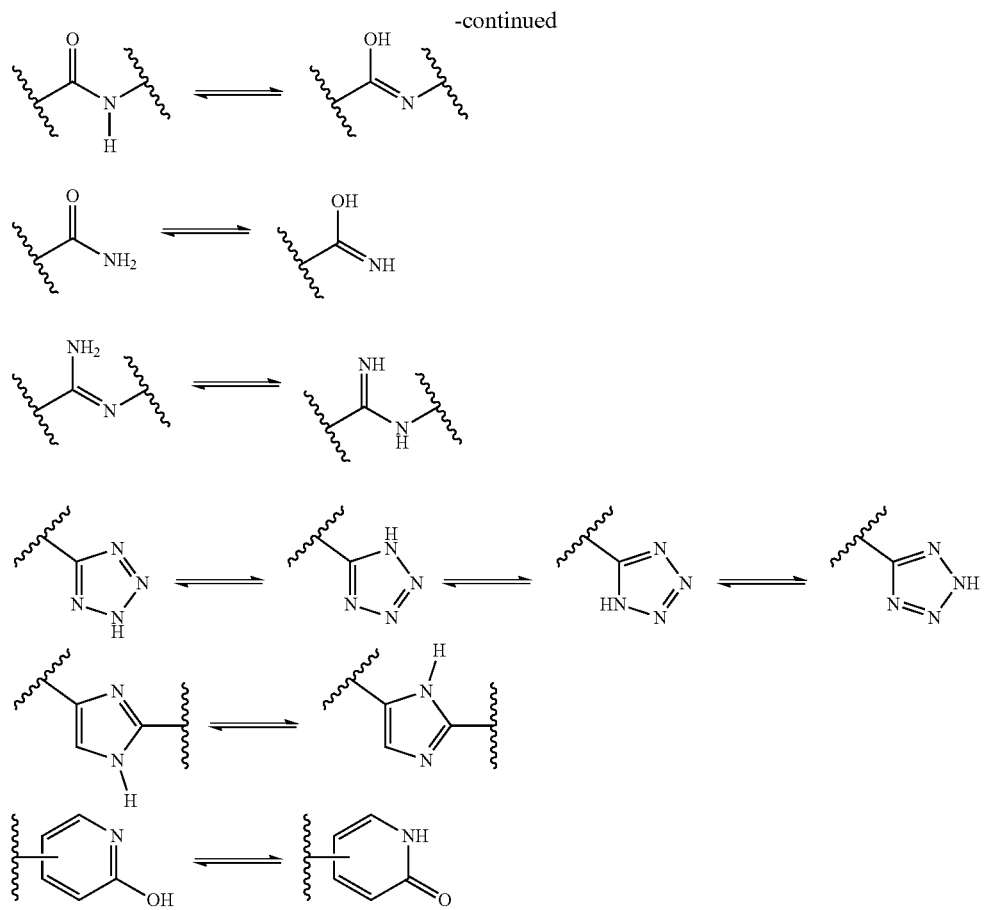

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility, or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include any suitable derivatives of alcohol or amine functional groups in the active compounds and the like that are known to a skilled practitioner. Examples of any suitable derivatives include but are not limited to acetate, formate, and benzoate derivatives of alcohol or amine functional groups.

As used herein, "treatment" or "treating" or "palliating" or "ameliorating" are used interchangeably herein. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compound 1

In some embodiments is a compound that is Compound 1 having the structure:

Compound 1

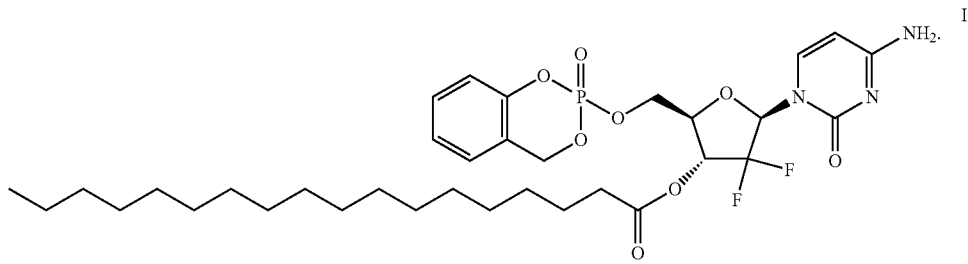

Preparation of Compound 1

Compound 1 described herein is made according to organic synthesis techniques, starting from commercially available chemicals and/or from compounds described in the chemical literature. "Commercially available chemicals" are obtained from standard commercial sources including, but not limited to, Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J.C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C.). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, compounds described herein are synthesized as described in PCT/US18/44389, which is hereby incorporated by reference in its entirety.

Prodrugs

Compound 1 described herein is a prodrug. A "prodrug" refers to an agent that is converted into the parent drug in vivo. Prodrugs are often useful because, in some situations, they are easier to administer than the parent drug. In some embodiments, the prodrug is a substrate for a transporter. In some embodiments, the prodrug also has improved solubility in pharmaceutical compositions over the parent drug. In some embodiments, the design of a prodrug increases the effective water solubility. In some embodiments, the design of a prodrug decreases the effective water solubility. An example, without limitation, of a prodrug is a compound described herein, which is administered as an ester (the "prodrug") but then is metabolically hydrolyzed to provide the active entity. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound. In certain embodiments Compound 1 is metabolized to gemcitabine monophosphate.

Compound 1 described herein can be metabolized, in part, to release stearic acid, a C18 saturated fatty acid. Steric acid is one of the most common fatty acids in nature and is a component of many animal-derived and plant-derived fats. As such, the release of stearic acid in the metabolism of Compound 1 is well tolerated in animals, including humans. Conversely, the chemically close odd-chain numbered fatty acids margaric acid (C17) and nonadecylic acid (C19) are both found rarely in nature, with typically only trace quantities in the human diet.

Prodrugs include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191, and Bundgaard, H., Advanced Drug Delivery Review, 1992, 8, 1-38, each of which is incorporated herein by reference. In some embodiments, a hydroxyl group in the parent compound is incorporated into an acyloxyalkyl ester, alkoxycarbonyloxyalkyl ester, aryl ester, phosphate ester, sugar ester, ether, and the like.

Further Forms of Compound 1 Disclosed Herein

Isomers

Compound 1 described herein possesses more than one chiral centers and each center exists in the R configuration or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion, are useful for the applications described herein. In some embodiments, Compound 1 described herein is prepared as an optically pure enantiomer by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization. In some situations, Compound 1 exists as a tautomer. The compounds described herein include all possible tautomers within the Compound 1 formula described herein.

Labeled Compounds

In some embodiments, Compound 1 described herein exists in an isotopically-labeled form.

In some embodiments, the methods disclosed herein include methods of treating diseases by administering such isotopically-labeled compounds. In some embodiments, the methods disclosed herein include methods of treating diseases by administering such isotopically-labeled compound as a pharmaceutical composition. Thus, in some embodiments, Compound 1 disclosed herein includes isotopically-labeled compounds, which are identical to those recited herein, but for the fact that one or more atoms are replaced by an atom having an atomic mass or mass number different from the atomic mass or mass number usually found in nature. Examples of isotopes that are incorporated into Compound 1 described herein include isotopes of hydrogen, carbon, nitrogen, oxygen, phosphorous, sulfur, fluorine, and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compound 1 described herein, and pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i. e., $^{3}H$ and carbon-14, i. e., $^{14}C$, isotopes are particularly preferred for their ease of preparation and detectability. Further, substitution with heavy isotopes such as deuterium, i.e., 2H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, Compound 1 described herein exists as their pharmaceutically acceptable salt. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, Compound 1 described herein possess basic groups and therefore react with any of a number of inorganic and organic acids, to form a pharmaceutically acceptable salt. In some embodiments, these salts are prepared in situ during the final isolation and purification of Compound 1 described herein, or by separately reacting purified Compound 1 in its free form with a suitable acid, and isolating the salt thus formed.

Solvates

In some embodiments, Compound 1 described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of Compound 1 described herein are conveniently prepared by recrystallization from an aqueous/organic solvent mixture, using organic solvents including, but not limited to, dioxane, tetrahydrofuran or MeOH. In some embodiments, Compound 1 provided herein exists in unsolvated as well as solvated forms. In general, the solvated forms are considered equivalent to the unsolvated forms for the purposes of the compounds and methods provided herein.

Pharmaceutically Acceptable Carrier

In some embodiments, the composition described herein also comprise a pharmaceutically acceptable carrier. In some embodiments, the pharmaceutically acceptable carrier is a protein. The term "protein' as used herein refers to polypeptides or polymers comprising of amino acids of any length (including full length or fragments). These polypeptides or polymers are linear or branched, comprise modified amino acids, and/or are interrupted by non-amino acids. The term also encompasses an amino acid polymer that has been modified by natural means or by chemical modification. Examples of chemical modifications include, but are not limited to, disulfide bond formation, glycosylation, lipidation, acetylation, phosphorylation, or any other manipulation or modification. Also included within this term are, for example, polypeptides containing one or more analogs of an amino acid (including, for example, unnatural amino acids, etc.), as well as other modifications known in the art. The proteins described herein may be naturally occurring, i.e., obtained or derived from a natural source (such as blood), or synthesized (such as chemically synthesized or synthesized by recombinant DNA techniques). In some embodiments, the protein is naturally occurring. In some embodiments, the protein is obtained or derived from a natural source. In some embodiments, the protein is synthetically prepared.

Examples of suitable pharmaceutically acceptable carriers include proteins normally found in blood or plasma, such as albumin, immunoglobulin including IgA, lipoproteins, apolipoprotein B, alpha-acid glycoprotein, beta-2-macroglobulin, thyroglobulin, transferin, fibronectin, factor VII, factor VIII, factor IX, factor X, and the like. In some embodiments, the pharmaceutically acceptable carrier is a non-blood protein. Examples of non-blood protein include but are not limited to casein, C.-lactalbumin, and B-lactoglobulin.

In some embodiments, the pharmaceutically acceptable carrier is albumin. In some embodiments, the albumin is human serum albumin (HSA). Human serum albumin is the most abundant protein in human blood and is a highly soluble globular protein that consists of 585 amino acids and has a molecular weight of 66.5 kDa. Other albumins suitable for use include, but are not limited to, bovine serum albumin.

In some non-limiting embodiments, the composition described herein further comprises one or more albumin stabilizers. In some embodiments, the albumin stabilizer is N-acetyl tryptophan, octanoate, cholesterol, or a combination thereof.

In some embodiments, the molar ratio of the compound to pharmaceutically acceptable carrier is from about 1:1 to about 40:1. In some embodiments, the molar ratio of the compound to pharmaceutically acceptable carrier is from about 1:1 to about 20:1. In some embodiments, the molar ratio of the compound to pharmaceutically acceptable carrier is from about 2:1 to about 12:1.

In some embodiments, the molar ratio of the compound to pharmaceutically acceptable carrier is about 40:1. In some embodiments, the molar ratio of the compound to pharmaceutically acceptable carrier is about 35:1. In some embodiments, the molar ratio of the compound to pharmaceutically acceptable carrier is about 30:1. In some embodiments, the molar ratio of the compound to pharmaceutically acceptable carrier is about 25:1. In some embodiments, the molar ratio of the compound to pharmaceutically acceptable carrier is about 20:1. In some embodiments, the molar ratio of the compound to pharmaceutically acceptable carrier is about 19:1. In some embodiments, the molar ratio of the compound to pharmaceutically acceptable carrier is about 18:1. In some embodiments, the molar ratio of the compound to pharmaceutically acceptable carrier is about 17:1. In some embodiments, the molar ratio of the compound to pharmaceutically acceptable carrier is about 16:1. In some embodiments, the molar ratio of the compound to pharmaceutically acceptable carrier is about 15:1. In some embodiments, the molar ratio of the compound to pharmaceutically acceptable carrier is about 14:1. In some embodiments, the molar ratio of the compound to pharmaceutically acceptable carrier is about 13:1. In some embodiments, the molar ratio of the compound to pharmaceutically acceptable carrier is about 12:1. In some embodiments, the molar ratio of the compound to pharmaceutically acceptable carrier is about 11:1. In some embodiments, the molar ratio of the compound to pharmaceutically acceptable carrier is about 10:1. In some embodiments, the molar ratio of the compound to pharmaceutically acceptable carrier is about 9:1. In some embodiments, the molar ratio of the compound to pharmaceutically acceptable carrier is about 8:1. In some embodiments, the molar ratio of the compound to pharmaceutically acceptable carrier is about 7:1. In some embodiments, the molar ratio of the compound to pharmaceutically acceptable carrier is about 6:1. In some embodiments, the molar ratio of the compound to pharmaceutically acceptable carrier is about 5:1. In some embodiments, the molar ratio of the compound to pharmaceutically acceptable carrier is about 4:1. In some embodiments, the molar ratio of the compound to pharmaceutically acceptable carrier is about 3:1. In some embodiments, the molar ratio of the compound to pharmaceutically acceptable carrier is about 2:1. In some embodiments, the molar ratio of the compound to pharmaceutically acceptable carrier is about 1:1.

Nanoparticles

Described herein in one aspect is a composition comprising nanoparticles comprising Compound 1 and a pharmaceutically acceptable carrier. In another aspect described herein is a composition comprising nanoparticles comprising Compound 1 and a pharmaceutically acceptable carrier, wherein the pharmaceutically acceptable carrier is albumin.

In some embodiments, the nanoparticles have an average diameter of about 1000 nm or less for a predetermined amount of time after nanoparticle formation. In some embodiments, the nanoparticles have an average diameter of about 950 nm or less for a predetermined amount of time after nanoparticle formation. In some embodiments, the nanoparticles have an average diameter of about 900 nm or less for a predetermined amount of time after nanoparticle formation. In some embodiments, the nanoparticles have an average diameter of about 850 nm or less for a predetermined amount of time after nanoparticle formation. In some embodiments, the nanoparticles have an average diameter of about 800 nm or less for a predetermined amount of time after nanoparticle formation. In some embodiments, the nanoparticles have an average diameter of about 750 nm or less for a predetermined amount of time after nanoparticle formation. In some embodiments, the nanoparticles have an average diameter of about 700 nm or less for a predetermined amount of time after nanoparticle formation. In some embodiments, the nanoparticles have an average diameter of about 650 nm or less for a predetermined amount of time after nanoparticle formation. In some embodiments, the nanoparticles have an average diameter of about 600 nm or less for a predetermined amount of time after nanoparticle formation. In some embodiments, the nanoparticles have an average diameter of about 550 nm or less for a predetermined amount of time after nanoparticle formation. In some embodiments, the nanoparticles have an average diameter of about 500 nm or less for a predetermined amount of time after nanoparticle formation. In some embodiments, the nanoparticles have an average diameter of about 450 nm or less for a predetermined amount of time after nanoparticle formation. In some embodiments, the nanoparticles have an average diameter of about 400 nm or less for a predetermined amount of time after nanoparticle formation. In some embodiments, the nanoparticles have an average diameter of about 350 nm or less for a predetermined amount of time after nanoparticle formation. In some embodiments, the nanoparticles have an average diameter of about 300 nm or less for a predetermined amount of time after nanoparticle formation. In some embodiments, the nanoparticles have an average diameter of about 250 nm or less for a predetermined amount of time after nanoparticle formation. In some embodiments, the nanoparticles have an average diameter of about 240 nm or less for a predetermined amount of time after nanoparticle formation. In some embodiments, the nanoparticles have an average diameter of about 230 nm or less for a predetermined amount of time after nanoparticle formation. In some embodiments, the nanoparticles have an average diameter of about 220 nm or less for a predetermined amount of time after nanoparticle formation. In some embodiments, the nanoparticles have an average diameter of about 210 nm or less for a predetermined amount of time after nanoparticle formation. In some embodiments, the nanoparticles have an average diameter of about 200 nm or less for a predetermined amount of time after nanoparticle formation. In some embodiments, the nanoparticles have an average diameter of about 190 nm or less for a predetermined amount of time after nanoparticle formation. In some embodiments, the nanoparticles have an average diameter of about 180 nm or less for a predetermined amount of time after nanoparticle formation. In some embodiments, the nanoparticles have an average diameter of about 170 nm or less for a predetermined amount of time after nanoparticle formation. In some embodiments, the nanoparticles have an average diameter of about 160 nm or less for a predetermined amount of time after nanoparticle formation. In some embodiments, the nanoparticles have an average diameter of about 150 nm or less for a predetermined amount of time after nanoparticle formation. In some embodiments, the nanoparticles have an average diameter of about 140 nm or less for a predetermined amount of time after nanoparticle formation. In some embodiments, the nanoparticles have an average diameter of about 130 nm or less for a predetermined amount of time after nanoparticle formation. In some embodiments, the nanoparticles have an average diameter of about 120 nm or less for a predetermined amount of time after nanoparticle formation. In some embodiments, the nanoparticles have an average diameter of about 110 nm or less for a predetermined amount of time after nanoparticle formation. In some embodiments, the nanoparticles have an average diameter of about 100 nm or less for a predetermined amount of time after nanoparticle formation. In some embodiments, the nanoparticles have an average diameter of about 90 nm or less for a predetermined amount of time after nanoparticle formation. In some embodiments, the nanoparticles have an average diameter of about 80 nm or less for a predetermined amount of time after nanoparticle formation. In some embodiments, the nanoparticles have an average diameter of about 70 nm or less for a predetermined amount of time after nanoparticle formation. In some embodiments, the nanoparticles have an average diameter of about 60 nm or less for a predetermined amount of time after nanoparticle formation. In some embodiments, the nanoparticles have an average diameter of about 50 nm or less for a predetermined amount of time after nanoparticle formation. In some embodiments, the nanoparticles have an average diameter of about 40 nm or less for a predetermined amount of time after nanoparticle formation. In some embodiments, the nanoparticles have an average diameter of about 30 nm or less for a predetermined amount of time after nanoparticle formation. In some embodiments, the nanoparticles have an average diameter of about 20 nm or less for a predetermined amount of time after nanoparticle formation. In some embodiments, the nanoparticles have an average diameter of about 10 nm or less for a predetermined amount of time after nanoparticle formation.

In some embodiments, the nanoparticles have an average diameter of about 10 nm or greater for a predetermined amount of time after nanoparticle formation. In some embodiments, the nanoparticles have an average diameter of about 20 nm or greater for a predetermined amount of time after nanoparticle formation. In some embodiments, the nanoparticles have an average diameter of about 30 nm or greater for a predetermined amount of time after nanoparticle formation. In some embodiments, the nanoparticles have an average diameter of about 40 nm or greater for a predetermined amount of time after nanoparticle formation. In some embodiments, the nanoparticles have an average diameter of about 50 nm or greater for a predetermined amount of time after nanoparticle formation. In some embodiments, the nanoparticles have an average diameter of about 60 nm or greater for a predetermined amount of time after nanoparticle formation. In some embodiments, the nanoparticles have an average diameter of about 70 nm or greater for a predetermined amount of time after nanoparticle formation. In some embodiments, the nanoparticles have an average diameter of about 80 nm or greater for a predetermined amount of time after nanoparticle formation. In some embodiments, the nanoparticles have an average diameter of about 90 nm or greater for a predetermined amount of time after nanoparticle formation. In some embodiments, the nanoparticles have an average diameter of about 100 nm or greater for a predetermined amount of time after nanoparticle formation. In some embodiments, the nanoparticles have an average diameter of about 110 nm or greater for a predetermined amount of time after nanoparticle formation. In some embodiments, the nanoparticles have an average diameter of about 120 nm or greater for a predetermined amount of time after nanoparticle formation. In some embodiments, the nanoparticles have an average diameter of about 130 nm or greater for a predetermined amount of time after nanoparticle formation. In some embodiments, the nanoparticles have an average diameter of about 140 nm or greater for a predetermined amount of time after nanoparticle formation. In some embodiments, the nanoparticles have an average diameter of about 150 nm or greater for a predetermined amount of time after nanoparticle formation. In some embodiments, the nanoparticles have an average diameter of about 160 nm or greater for a predetermined amount of time after nanoparticle formation.

In some embodiments, the nanoparticles have an average diameter of about 170 nm or greater for a predetermined amount of time after nanoparticle formation. In some embodiments, the nanoparticles have an average diameter of about 180 nm or greater for a predetermined amount of time after nanoparticle formation. In some embodiments, the nanoparticles have an average diameter of about 190 nm or greater for a predetermined amount of time after nanoparticle formation. In some embodiments, the nanoparticles have an average diameter of about 200 nm or greater for a predetermined amount of time after nanoparticle formation. In some embodiments, the nanoparticles have an average diameter of about 210 nm or greater for a predetermined amount of time after nanoparticle formation. In some embodiments, the nanoparticles have an average diameter of about 220 nm or greater for a predetermined amount of time after nanoparticle formation. In some embodiments, the nanoparticles have an average diameter of about 230 nm or greater for a predetermined amount of time after nanoparticle formation. In some embodiments, the nanoparticles have an average diameter of about 240 nm or greater for a predetermined amount of time after nanoparticle formation. In some embodiments, the nanoparticles have an average diameter of about 250 nm or greater for a predetermined amount of time after nanoparticle formation. In some embodiments, the nanoparticles have an average diameter of about 300 nm or greater for a predetermined amount of time after nanoparticle formation. In some embodiments, the nanoparticles have an average diameter of about 350 nm or greater for a predetermined amount of time after nanoparticle formation. In some embodiments, the nanoparticles have an average diameter of about 400 nm or greater for a predetermined amount of time after nanoparticle formation. In some embodiments, the nanoparticles have an average diameter of about 450 nm or greater for a predetermined amount of time after nanoparticle formation. In some embodiments, the nanoparticles have an average diameter of about 500 nm or greater for a predetermined amount of time after nanoparticle formation. In some embodiments, the nanoparticles have an average diameter of about 550 nm or greater for a predetermined amount of time after nanoparticle formation. In some embodiments, the nanoparticles have an average diameter of about 600 nm or greater for a predetermined amount of time after nanoparticle formation. In some embodiments, the nanoparticles have an average diameter of about 650 nm or greater for a predetermined amount of time after nanoparticle formation. In some embodiments, the nanoparticles have an average diameter of about 700 nm or greater for a predetermined amount of time after nanoparticle formation. In some embodiments, the nanoparticles have an average diameter of about 750 nm or greater for a predetermined amount of time after nanoparticle formation. In some embodiments, the nanoparticles have an average diameter of about 800 nm or greater for a predetermined amount of time after nanoparticle formation. In some embodiments, the nanoparticles have an average diameter of about 850 nm or greater for a predetermined amount of time after nanoparticle formation. In some embodiments, the nanoparticles have an average diameter of about 900 nm or greater for a predetermined amount of time after nanoparticle formation. In some embodiments, the nanoparticles have an average diameter of about 950 nm or greater for a predetermined amount of time after nanoparticle formation In some embodiments, the nanoparticles have an average diameter of from about 10 nm to about 1000 nm for a predetermined amount of time after nanoparticle formation. In some embodiments, the nanoparticles have an average diameter of from about 10 nm to about 950 nm for a predetermined amount of time after nanoparticle formation. In some embodiments, the nanoparticles have an average diameter of from about 10 nm to about 900 nm for a predetermined amount of time after nanoparticle formation. In some embodiments, the nanoparticles have an average diameter of from about 10 nm to about 850 nm for a predetermined amount of time after nanoparticle formation. In some embodiments, the nanoparticles have an average diameter of from about 10 nm to about 800 nm for a predetermined amount of time after nanoparticle formation. In some embodiments, the nanoparticles have an average diameter of from about 10 nm to about 750 nm for a predetermined amount of time after nanoparticle formation. In some embodiments, the nanoparticles have an average diameter of from about 10 nm to about 700 nm for a predetermined amount of time after nanoparticle formation. In some embodiments, the nanoparticles have an average diameter of from about 10 nm to about 650 nm for a predetermined amount of time after nanoparticle formation. In some embodiments, the nanoparticles have an average diameter of from about 10 nm to about 600 nm for a predetermined amount of time after nanoparticle formation. In some embodiments, the nanoparticles have an average diameter of from about 10 nm to about 550 nm for a predetermined amount of time after nanoparticle formation for a predetermined amount of time after nanoparticle formation. In some embodiments, the nanoparticles have an average diameter of from about 10 nm to about 500 nm for a predetermined amount of time after nanoparticle formation. In some embodiments, the nanoparticles have an average diameter of from about 10 nm to about 450 nm for a predetermined amount of time after nanoparticle formation. In some embodiments, the nanoparticles have an average diameter of from about 10 nm to about 400 nm for a predetermined amount of time after nanoparticle formation. In some embodiments, the nanoparticles have an average diameter of from about 10 nm to about 350 nm for a predetermined amount of time after nanoparticle formation. In some embodiments, the nanoparticles have an average diameter of from about 10 nm to about 300 nm for a predetermined amount of time after nanoparticle formation. In some embodiments, the nanoparticles have an average diameter of from about 10 nm to about 250 nm for a predetermined amount of time after nanoparticle formation. In some embodiments, the nanoparticles have an average diameter of from about 10 nm to about 240 nm for a predetermined amount of time after nanoparticle formation. In some embodiments, the nanoparticles have an average diameter of from about 10 nm to about 230 nm for a predetermined amount of time after nanoparticle formation. In some embodiments, the nanoparticles have an average diameter of from about 10 nm to about 220 nm for a predetermined amount of time after nanoparticle formation. In some embodiments, the nanoparticles have an average diameter of from about 10 nm to about 210 nm for a predetermined amount of time after nanoparticle formation. In some embodiments, the nanoparticles have an average diameter of from about 10 nm to about 200 nm for a predetermined amount of time after nanoparticle formation. In some embodiments, the nanoparticles have an average diameter of from about 10 nm to about 190 nm for a predetermined amount of time after nanoparticle formation. In some embodiments, the nanoparticles have an average diameter of from about 10 nm to about 180 nm for a predetermined amount of time after nanoparticle formation.

In some embodiments, the nanoparticles have an average diameter of from about 10 nm to about 170 nm for a predetermined amount of time after nanoparticle formation. In some embodiments, the nanoparticles have an average diameter of from about 10 nm to about 160 nm for a predetermined amount of time after nanoparticle formation. In some embodiments, the nanoparticles have an average diameter of from about 10 nm to about 150 nm for a predetermined amount of time after nanoparticle formation. In some embodiments, the nanoparticles have an average diameter of from about 10 nm to about 140 nm for a predetermined amount of time after nanoparticle formation. In some embodiments, the nanoparticles have an average diameter of from about 10 nm to about 130 nm for a predetermined amount of time after nanoparticle formation. In some embodiments, the nanoparticles have an average diameter of from about 10 nm to about 120 nm for a predetermined amount of time after nanoparticle formation. In some embodiments, the nanoparticles have an average diameter of from about 10 nm to about 110 nm for a predetermined amount of time after nanoparticle formation. In some embodiments, the nanoparticles have an average diameter of from about 10 nm to about 100 nm for a predetermined amount of time after nanoparticle formation. In some embodiments, the nanoparticles have an average diameter of from about 10 nm to about 90 nm for a predetermined amount of time after nanoparticle formation. In some embodiments, the nanoparticles have an average diameter of from about 10 nm to about 80 nm for a predetermined amount of time after nanoparticle formation. In some embodiments, the nanoparticles have an average diameter of from about 10 nm to about 70 nm for a predetermined amount of time after nanoparticle formation. In some embodiments, the nanoparticles have an average diameter of from about 10 nm to about 60 nm for a predetermined amount of time after nanoparticle formation. In some embodiments, the nanoparticles have an average diameter of from about 10 nm to about 50 nm for a predetermined amount of time after nanoparticle formation. In some embodiments, the nanoparticles have an average diameter of from about 10 nm to about 40 nm for a predetermined amount of time after nanoparticle formation. In some embodiments, the nanoparticles have an average diameter of from about 10 nm to about 30 nm for a predetermined amount of time after nanoparticle formation. In some embodiments, the nanoparticles have an average diameter of from about 10 nm to about 20 nm for a predetermined amount of time after nanoparticle formation.

In some embodiments, the nanoparticles have an average diameter of about 10 nm for a predetermined amount of time after nanoparticle formation. In some embodiments, the nanoparticles have an average diameter of about 20 nm for a predetermined amount of time after nanoparticle formation. In some embodiments, the nanoparticles have an average diameter of about 30 nm for a predetermined amount of time after nanoparticle formation. In some embodiments, the nanoparticles have an average diameter of about 40 nm for a predetermined amount of time after nanoparticle formation. In some embodiments, the nanoparticles have an average diameter of about 50 nm for a predetermined amount of time after nanoparticle formation. In some embodiments, the nanoparticles have an average diameter of about 60 nm for a predetermined amount of time after nanoparticle formation. In some embodiments, the nanoparticles have an average diameter of about 70 nm for a predetermined amount of time after nanoparticle formation. In some embodiments, the nanoparticles have an average diameter of about 80 nm for a predetermined amount of time after nanoparticle formation. In some embodiments, the nanoparticles have an average diameter of about 90 nm for a predetermined amount of time after nanoparticle formation. In some embodiments, the nanoparticles have an average diameter of about 100 nm for a predetermined amount of time after nanoparticle formation. In some embodiments, the nanoparticles have an average diameter of about 110 nm for a predetermined amount of time after nanoparticle formation. In some embodiments, the nanoparticles have an average diameter of about 120 nm for a predetermined amount of time after nanoparticle formation. In some embodiments, the nanoparticles have an average diameter of about 130 nm for a predetermined amount of time after nanoparticle formation. In some embodiments, the nanoparticles have an average diameter of about 140 nm for a predetermined amount of time after nanoparticle formation. In some embodiments, the nanoparticles have an average diameter of about 150 nm for a predetermined amount of time after nanoparticle formation. In some embodiments, the nanoparticles have an average diameter of about 160 nm for a predetermined amount of time after nanoparticle formation. In some embodiments, the nanoparticles have an average diameter of about 170 nm for a predetermined amount of time after nanoparticle formation. In some embodiments, the nanoparticles have an average diameter of about 180 nm for a predetermined amount of time after nanoparticle formation. In some embodiments, the nanoparticles have an average diameter of about 190 nm for a predetermined amount of time after nanoparticle formation. In some embodiments, the nanoparticles have an average diameter of about 200 nm for a predetermined amount of time after nanoparticle formation. In some embodiments, the nanoparticles have an average diameter of about 210 nm for a predetermined amount of time after nanoparticle formation. In some embodiments, the nanoparticles have an average diameter of about 220 nm for a predetermined amount of time after nanoparticle formation. In some embodiments, the nanoparticles have an average diameter of about 230 nm for a predetermined amount of time after nanoparticle formation. In some embodiments, the nanoparticles have an average diameter of about 240 nm for a predetermined amount of time after nanoparticle formation. In some embodiments, the nanoparticles have an average diameter of about 250 nm for a predetermined amount of time after nanoparticle formation. In some embodiments, the nanoparticles have an average diameter of about 300 nm for a predetermined amount of time after nanoparticle formation. In some embodiments, the nanoparticles have an average diameter of about 350 nm for a predetermined amount of time after nanoparticle formation. In some embodiments, the nanoparticles have an average diameter of about 400 nm for a predetermined amount of time after nanoparticle formation. In some embodiments, the nanoparticles have an average diameter of about 450 nm for a predetermined amount of time after nanoparticle formation. In some embodiments, the nanoparticles have an average diameter of about 500 nm for a predetermined amount of time after nanoparticle formation. In some embodiments, the nanoparticles have an average diameter of about 550 nm for a predetermined amount of time after nanoparticle formation. In some embodiments, the nanoparticles have an average diameter of about 600 nm for a predetermined amount of time after nanoparticle formation. In some embodiments, the nanoparticles have an average diameter of about 650 nm for a predetermined amount of time after nanoparticle formation. In some embodiments, the nanoparticles have an average diameter of about 700 nm for a predetermined amount of time after nanoparticle formation. In some embodiments, the nanoparticles have an average diameter of about 750 nm for a predetermined amount of time after nanoparticle formation. In some embodiments, the nanoparticles have an average diameter of about 800 nm for a predetermined amount of time after nanoparticle formation. In some embodiments, the nanoparticles have an average diameter of about 850 nm for a predetermined amount of time after nanoparticle formation. In some embodiments, the nanoparticles have an average diameter of about 900 nm for a predetermined amount of time after nanoparticle formation. In some embodiments, the nanoparticles have an average diameter of about 950 nm for a predetermined amount of time after nanoparticle formation. In some embodiments, the nanoparticles have an average diameter of about 1000 nm for a predetermined amount of time after nanoparticle formation.

In some embodiments, the predetermined amount of time is at least about 15 minutes. In some embodiments, the predetermined amount of time is at least about 30 minutes. In some embodiments, the predetermined amount of time is at least about 45 minutes. In some embodiments, the predetermined amount of time is at least about 1 hour. In some embodiments, the predetermined amount of time is at least about 2 hours. In some embodiments, the predetermined amount of time is at least about 3 hours. In some embodiments, the predetermined amount of time is at least about 4 hours. In some embodiments, the predetermined amount of time is at least about 5 hours. In some embodiments, the predetermined amount of time is at least about 6 hours. In some embodiments, the predetermined amount of time is at least about 7 hours. In some embodiments, the predetermined amount of time is at least about 8 hours. In some embodiments, the predetermined amount of time is at least about 9 hours. In some embodiments, the predetermined amount of time is at least about 10 hours. In some embodiments, the predetermined amount of time is at least about 11 hours. In some embodiments, the predetermined amount of time is at least about 12 hours. In some embodiments, the predetermined amount of time is at least about 1 day. In some embodiments, the predetermined amount of time is at least about 2 days. In some embodiments, the predetermined amount of time is at least about 3 days. In some embodiments, the predetermined amount of time is at least about 4 days. In some embodiments, the predetermined amount of time is at least about 5 days. In some embodiments, the predetermined amount of time is at least about 6 days. In some embodiments, the predetermined amount of time is at least about 7 days. In some embodiments, the predetermined amount of time is at least about 14 days. In some embodiments, the predetermined amount of time is at least about 21 days. In some embodiments, the predetermined amount of time is at least about 30 days.

In some embodiments, the predetermined amount of time is from about 15 minutes to about 30 days. In some embodiments, the predetermined amount of time is about 30 minutes to about 30 days. In some embodiments, the predetermined amount of time is from about 45 minutes to about 30 days. In some embodiments, the predetermined amount of time is from about 1 hour to about 30 days. In some embodiments, the predetermined amount of time is from about 2 hours to about 30 days. In some embodiments, the predetermined amount of time is from about 3 hours to about 30 days. In some embodiments, the predetermined amount of time is from about 4 hours to about 30 days. In some embodiments, the predetermined amount of time is from about 5 hours to about 30 days. In some embodiments, the predetermined amount of time is from about 6 hours to about 30 days. In some embodiments, the predetermined amount of time is from about 7 hours to about 30 days. In some embodiments, the predetermined amount of time is from about 8 hours to about 30 days. In some embodiments, the predetermined amount of time is from about 9 hours to about 30 days. In some embodiments, the predetermined amount of time is from about 10 hours to about 30 days. In some embodiments, the predetermined amount of time is from about 11 hours to about 30 days. In some embodiments, the predetermined amount of time is from about 12 hours to about 30 days. In some embodiments, the predetermined amount of time is from about 1 day to about 30 days. In some embodiments, the predetermined amount of time is from about 2 days to about 30 days. In some embodiments, the predetermined amount of time is from about 3 days to about 30 days. In some embodiments, the predetermined amount of time is from about 4 days to about 30 days. In some embodiments, the predetermined amount of time is from about 5 days to about 30 days. In some embodiments, the predetermined amount of time is from about 6 days to about 30 days. In some embodiments, the predetermined amount of time is from about 7 days to about 30 days. In some embodiments, the predetermined amount of time is from about 14 days to about 30 days. In some embodiments, the predetermined amount of time is from about 21 days to about 30 days.

In some embodiments, the nanoparticles have an average diameter of about 1000 nm or less for at least about 15 minutes after nanoparticle formation. In some embodiments, the nanoparticles have an average diameter of about 950 nm or less for at least about 15 minutes after nanoparticle formation. In some embodiments, the nanoparticles have an average diameter of about 900 nm or less for at least about 15 minutes after nanoparticle formation. In some embodiments, the nanoparticles have an average diameter of about 850 nm or less for at least about 15 minutes after nanoparticle formation. In some embodiments, the nanoparticles have an average diameter of about 800 nm or less for at least about 15 minutes after nanoparticle formation. In some embodiments, the nanoparticles have an average diameter of about 750 nm or less for at least about 15 minutes after nanoparticle formation. In some embodiments, the nanoparticles have an average diameter of about 700 nm or less for at least about 15 minutes after nanoparticle formation. In some embodiments, the nanoparticles have an average diameter of about 650 nm or less for at least about 15 minutes after nanoparticle formation. In some embodiments, the nanoparticles have an average diameter of about 600 nm or less for at least about 15 minutes after nanoparticle formation. In some embodiments, the nanoparticles have an average diameter of about 550 nm or less for at least about 15 minutes after nanoparticle formation. In some embodiments, the nanoparticles have an average diameter of about 500 nm or less for at least about 15 minutes after nanoparticle formation. In some embodiments, the nanoparticles have an average diameter of about 450 nm or less for at least about 15 minutes after nanoparticle formation. In some embodiments, the nanoparticles have an average diameter of about 400 nm or less for at least about 15 minutes after nanoparticle formation. In some embodiments, the nanoparticles have an average diameter of about 350 nm or less for at least about 15 minutes after nanoparticle formation. In some embodiments, the nanoparticles have an average diameter of about 300 nm or less for at least about 15 minutes after nanoparticle formation. In some embodiments, the nanoparticles have an average diameter of about 250 nm or less for at least about 15 minutes after nanoparticle formation. In some embodiments, the nanoparticles have an average diameter of about 240 nm or less for at least about 15 minutes after nanoparticle formation. In some embodiments, the nanoparticles have an average diameter of about 230 nm or less for at least about 15 minutes after nanoparticle formation. In some embodiments, the nanoparticles have an average diameter of about 220 nm or less for at least about 15 minutes after nanoparticle formation. In some embodiments, the nanoparticles have an average diameter of about 210 nm or less for at least about 15 minutes after nanoparticle formation. In some embodiments, the nanoparticles have an average diameter of about 200 nm or less for at least about 15 minutes after nanoparticle formation. In some embodiments, the nanoparticles have an average diameter of about 190 nm or less for at least about 15 minutes after nanoparticle formation. In some embodiments, the nanoparticles have an average diameter of about 180 nm or less for at least about 15 minutes after nanoparticle formation. In some embodiments, the nanoparticles have an average diameter of about 170 nm or less for at least about 15 minutes after nanoparticle formation. In some embodiments, the nanoparticles have an average diameter of about 160 nm or less for at least about 15 minutes after nanoparticle formation. In some embodiments, the nanoparticles have an average diameter of about 150 nm or less for at least about 15 minutes after nanoparticle formation. In some embodiments, the nanoparticles have an average diameter of about 140 nm or less for at least about 15 minutes after nanoparticle formation. In some embodiments, the nanoparticles have an average diameter of about 130 nm or less for at least about 15 minutes after nanoparticle formation. In some embodiments, the nanoparticles have an average diameter of about 120 nm or less for at least about 15 minutes after nanoparticle formation. In some embodiments, the nanoparticles have an average diameter of about 110 nm or less for at least about 15 minutes after nanoparticle formation. In some embodiments, the nanoparticles have an average diameter of about 100 nm or less for at least about 15 minutes after nanoparticle formation. In some embodiments, the nanoparticles have an average diameter of about 90 nm or less for at least about 15 minutes after nanoparticle formation. In some embodiments, the nanoparticles have an average diameter of about 80 nm or less for at least about 15 minutes after nanoparticle formation. In some embodiments, the nanoparticles have an average diameter of about 70 nm or less for at least about 15 minutes after nanoparticle formation. In some embodiments, the nanoparticles have an average diameter of about 60 nm or less for at least about 15 minutes after nanoparticle formation. In some embodiments, the nanoparticles have an average diameter of about 50 nm or less for at least about 15 minutes after nanoparticle formation. In some embodiments, the nanoparticles have an average diameter of about 40 nm or less for at least about 15 minutes after nanoparticle formation. In some embodiments, the nanoparticles have an average diameter of about 30 nm or less for at least about 15 minutes after nanoparticle formation. In some embodiments, the nanoparticles have an average diameter of about 20 nm or less for at least about 15 minutes after nanoparticle formation. In some embodiments, the nanoparticles have an average diameter of about 10 nm or less for at least about 15 minutes after nanoparticle formation.

In some embodiments, the nanoparticles have an average diameter of about 10 nm or greater for at least about 15 minutes after nanoparticle formation. In some embodiments, the nanoparticles have an average diameter of about 20 nm or greater for at least about 15 minutes after nanoparticle formation. In some embodiments, the nanoparticles have an average diameter of about 30 nm or greater for at least about 15 minutes after nanoparticle formation. In some embodiments, the nanoparticles have an average diameter of about 40 nm or greater for at least about 15 minutes after nanoparticle formation. In some embodiments, the nanoparticles have an average diameter of about 50 nm or greater for at least about 15 minutes after nanoparticle formation. In some embodiments, the nanoparticles have an average diameter of about 60 nm or greater for at least about 15 minutes after nanoparticle formation. In some embodiments, the nanoparticles have an average diameter of about 70 nm or greater for at least about 15 minutes after nanoparticle formation. In some embodiments, the nanoparticles have an average diameter of about 80 nm or greater for at least about 15 minutes after nanoparticle formation. In some embodiments, the nanoparticles have an average diameter of about 90 nm or greater for at least about 15 minutes after nanoparticle formation. In some embodiments, the nanoparticles have an average diameter of about 100 nm or greater for at least about 15 minutes after nanoparticle formation. In some embodiments, the nanoparticles have an average diameter of about 110 nm or greater for at least about 15 minutes after nanoparticle formation. In some embodiments, the nanoparticles have an average diameter of about 120 nm or greater for at least about 15 minutes after nanoparticle formation. In some embodiments, the nanoparticles have an average diameter of about 130 nm or greater for at least about 15 minutes after nanoparticle formation. In some embodiments, the nanoparticles have an average diameter of about 140 nm or greater for at least about 15 minutes after nanoparticle formation. In some embodiments, the nanoparticles have an average diameter of about 150 nm or greater for at least about 15 minutes after nanoparticle formation. In some embodiments, the nanoparticles have an average diameter of about 160 nm or greater for at least about 15 minutes after nanoparticle formation. In some embodiments, the nanoparticles have an average diameter of about 170 nm or greater for at least about 15 minutes after nanoparticle formation. In some embodiments, the nanoparticles have an average diameter of about 180 nm or greater for at least about 15 minutes after nanoparticle formation. In some embodiments, the nanoparticles have an average diameter of about 190 nm or greater for at least about 15 minutes after nanoparticle formation. In some embodiments, the nanoparticles have an average diameter of about 200 nm or greater for at least about 15 minutes after nanoparticle formation. In some embodiments, the nanoparticles have an average diameter of about 210 nm or greater for at least about 15 minutes after nanoparticle formation. In some embodiments, the nanoparticles have an average diameter of about 220 nm or greater for at least about 15 minutes after nanoparticle formation. In some embodiments, the nanoparticles have an average diameter of about 230 nm or greater for at least about 15 minutes after nanoparticle formation. In some embodiments, the nanoparticles have an average diameter of about 240 nm or greater for at least about 15 minutes after nanoparticle formation. In some embodiments, the nanoparticles have an average diameter of about 250 nm or greater for at least about 15 minutes after nanoparticle formation. In some embodiments, the nanoparticles have an average diameter of about 300 nm or greater for at least about 15 minutes after nanoparticle formation. In some embodiments, the nanoparticles have an average diameter of about 350 nm or greater for at least about 15 minutes after nanoparticle formation. In some embodiments, the nanoparticles have an average diameter of about 400 nm or greater for at least about 15 minutes after nanoparticle formation. In some embodiments, the nanoparticles have an average diameter of about 450 nm or greater for at least about 15 minutes after nanoparticle formation. In some embodiments, the nanoparticles have an average diameter of about 500 nm or greater for at least about 15 minutes after nanoparticle formation. In some embodiments, the nanoparticles have an average diameter of about 550 nm or greater for at least about 15 minutes after nanoparticle formation. In some embodiments, the nanoparticles have an average diameter of about 600 nm or greater for at least about 15 minutes after nanoparticle formation. In some embodiments, the nanoparticles have an average diameter of about 650 nm or greater for at least about 15 minutes after nanoparticle formation. In some embodiments, the nanoparticles have an average diameter of about 700 nm or greater for at least about 15 minutes after nanoparticle formation. In some embodiments, the nanoparticles have an average diameter of about 750 nm or greater for at least about 15 minutes after nanoparticle formation. In some embodiments, the nanoparticles have an average diameter of about 800 nm or greater for at least about 15 minutes after nanoparticle formation. In some embodiments, the nanoparticles have an average diameter of about 850 nm or greater for at least about 15 minutes after nanoparticle formation. In some embodiments, the nanoparticles have an average diameter of about 900 nm or greater for at least about 15 minutes after nanoparticle formation. In some embodiments, the nanoparticles have an average diameter of about 950 nm or greater for at least about 15 minutes after nanoparticle formation In some embodiments, the nanoparticles have an average diameter of from about 10 nm to about 1000 nm for at least about 15 minutes after nanoparticle formation. In some embodiments, the nanoparticles have an average diameter of from about 10 nm to about 950 nm for at least about 15 minutes after nanoparticle formation. In some embodiments, the nanoparticles have an average diameter of from about 10 nm to about 900 nm for at least about 15 minutes after nanoparticle formation. In some embodiments, the nanoparticles have an average diameter of from about 10 nm to about 850 nm for at least about 15 minutes after nanoparticle formation. In some embodiments, the nanoparticles have an average diameter of from about 10 nm to about 800 nm for at least about 15 minutes after nanoparticle formation. In some embodiments, the nanoparticles have an average diameter of from about 10 nm to about 750 nm for at least about 15 minutes after nanoparticle formation. In some embodiments, the nanoparticles have an average diameter of from about 10 nm to about 700 nm for at least about 15 minutes after nanoparticle formation. In some embodiments, the nanoparticles have an average diameter of from about 10 nm to about 650 nm for at least about 15 minutes after nanoparticle formation. In some embodiments, the nanoparticles have an average diameter of from about 10 nm to about 600 nm for at least about 15 minutes after nanoparticle formation. In some embodiments, the nanoparticles have an average diameter of from about 10 nm to about 550 nm for at least about 15 minutes after nanoparticle formation for at least about 15 minutes after nanoparticle formation. In some embodiments, the nanoparticles have an average diameter of from about 10 nm to about 500 nm for at least about 15 minutes after nanoparticle formation. In some embodiments, the nanoparticles have an average diameter of from about 10 nm to about 450 nm for at least about 15 minutes after nanoparticle formation. In some embodiments, the nanoparticles have an average diameter of from about 10 nm to about 400 nm for at least about 15 minutes after nanoparticle formation. In some embodiments, the nanoparticles have an average diameter of from about 10 nm to about 350 nm for at least about 15 minutes after nanoparticle formation. In some embodiments, the nanoparticles have an average diameter of from about 10 nm to about 300 nm for at least about 15 minutes after nanoparticle formation. In some embodiments, the nanoparticles have an average diameter of from about 10 nm to about 250 nm for at least about 15 minutes after nanoparticle formation. In some embodiments, the nanoparticles have an average diameter of from about 10 nm to about 240 nm for at least about 15 minutes after nanoparticle formation. In some embodiments, the nanoparticles have an average diameter of from about 10 nm to about 230 nm for at least about 15 minutes after nanoparticle formation. In some embodiments, the nanoparticles have an average diameter of from about 10 nm to about 220 nm for at least about 15 minutes after nanoparticle formation. In some embodiments, the nanoparticles have an average diameter of from about 10 nm to about 210 nm for at least about 15 minutes after nanoparticle formation. In some embodiments, the nanoparticles have an average diameter of from about 10 nm to about 200 nm for at least about 15 minutes after nanoparticle formation. In some embodiments, the nanoparticles have an average diameter of from about 10 nm to about 190 nm for at least about 15 minutes after nanoparticle formation. In some embodiments, the nanoparticles have an average diameter of from about 10 nm to about 180 nm for at least about 15 minutes after nanoparticle formation. In some embodiments, the nanoparticles have an average diameter of from about 10 nm to about 170 nm for at least about 15 minutes after nanoparticle formation. In some embodiments, the nanoparticles have an average diameter of from about 10 nm to about 160 nm for at least about 15 minutes after nanoparticle formation. In some embodiments, the nanoparticles have an average diameter of from about 10 nm to about 150 nm for at least about 15 minutes after nanoparticle formation. In some embodiments, the nanoparticles have an average diameter of from about 10 nm to about 140 nm for at least about 15 minutes after nanoparticle formation. In some embodiments, the nanoparticles have an average diameter of from about 10 nm to about 130 nm for at least about 15 minutes after nanoparticle formation. In some embodiments, the nanoparticles have an average diameter of from about 10 nm to about 120 nm for at least about 15 minutes after nanoparticle formation. In some embodiments, the nanoparticles have an average diameter of from about 10 nm to about 110 nm for at least about 15 minutes after nanoparticle formation. In some embodiments, the nanoparticles have an average diameter of from about 10 nm to about 100 nm for at least about 15 minutes after nanoparticle formation. In some embodiments, the nanoparticles have an average diameter of from about 10 nm to about 90 nm for at least about 15 minutes after nanoparticle formation. In some embodiments, the nanoparticles have an average diameter of from about 10 nm to about 80 nm for at least about 15 minutes after nanoparticle formation. In some embodiments, the nanoparticles have an average diameter of from about 10 nm to about 70 nm for at least about 15 minutes after nanoparticle formation. In some embodiments, the nanoparticles have an average diameter of from about 10 nm to about 60 nm for at least about 15 minutes after nanoparticle formation. In some embodiments, the nanoparticles have an average diameter of from about 10 nm to about 50 nm for at least about 15 minutes after nanoparticle formation. In some embodiments, the nanoparticles have an average diameter of from about 10 nm to about 40 nm for at least about 15 minutes after nanoparticle formation. In some embodiments, the nanoparticles have an average diameter of from about 10 nm to about 30 nm for at least about 15 minutes after nanoparticle formation. In some embodiments, the nanoparticles have an average diameter of from about 10 nm to about 20 nm for at least about 15 minutes after nanoparticle formation.

In some embodiments, the nanoparticles have an average diameter of about 10 nm for at least about 15 minutes after nanoparticle formation. In some embodiments, the nanoparticles have an average diameter of about 20 nm for at least about 15 minutes after nanoparticle formation. In some embodiments, the nanoparticles have an average diameter of about 30 nm for at least about 15 minutes after nanoparticle formation. In some embodiments, the nanoparticles have an average diameter of about 40 nm for at least about 15 minutes after nanoparticle formation. In some embodiments, the nanoparticles have an average diameter of about 50 nm for at least about 15 minutes after nanoparticle formation. In some embodiments, the nanoparticles have an average diameter of about 60 nm for at least about 15 minutes after nanoparticle formation. In some embodiments, the nanoparticles have an average diameter of about 70 nm for at least about 15 minutes after nanoparticle formation. In some embodiments, the nanoparticles have an average diameter of about 80 nm for at least about 15 minutes after nanoparticle formation. In some embodiments, the nanoparticles have an average diameter of about 90 nm for at least about 15 minutes after nanoparticle formation. In some embodiments, the nanoparticles have an average diameter of about 100 nm for at least about 15 minutes after nanoparticle formation. In some embodiments, the nanoparticles have an average diameter of about 110 nm for at least about 15 minutes after nanoparticle formation. In some embodiments, the nanoparticles have an average diameter of about 120 nm for at least about 15 minutes after nanoparticle formation. In some embodiments, the nanoparticles have an average diameter of about 130 nm for at least about 15 minutes after nanoparticle formation. In some embodiments, the nanoparticles have an average diameter of about 140 nm for at least about 15 minutes after nanoparticle formation. In some embodiments, the nanoparticles have an average diameter of about 150 nm for at least about 15 minutes after nanoparticle formation. In some embodiments, the nanoparticles have an average diameter of about 160 nm for at least about 15 minutes after nanoparticle formation. In some embodiments, the nanoparticles have an average diameter of about 170 nm for at least about 15 minutes after nanoparticle formation. In some embodiments, the nanoparticles have an average diameter of about 180 nm for at least about 15 minutes after nanoparticle formation. In some embodiments, the nanoparticles have an average diameter of about 190 nm for at least about 15 minutes after nanoparticle formation. In some embodiments, the nanoparticles have an average diameter of about 200 nm for at least about 15 minutes after nanoparticle formation. In some embodiments, the nanoparticles have an average diameter of about 210 nm for at least about 15 minutes after nanoparticle formation. In some embodiments, the nanoparticles have an average diameter of about 220 nm for at least about 15 minutes after nanoparticle formation. In some embodiments, the nanoparticles have an average diameter of about 230 nm for at least about 15 minutes after nanoparticle formation. In some embodiments, the nanoparticles have an average diameter of about 240 nm for at least about 15 minutes after nanoparticle formation. In some embodiments, the nanoparticles have an average diameter of about 250 nm for at least about 15 minutes after nanoparticle formation. In some embodiments, the nanoparticles have an average diameter of about 300 nm for at least about 15 minutes after nanoparticle formation. In some embodiments, the nanoparticles have an average diameter of about 350 nm for at least about 15 minutes after nanoparticle formation. In some embodiments, the nanoparticles have an average diameter of about 400 nm for at least about 15 minutes after nanoparticle formation. In some embodiments, the nanoparticles have an average diameter of about 450 nm for at least about 15 minutes after nanoparticle formation. In some embodiments, the nanoparticles have an average diameter of about 500 nm for at least about 15 minutes after nanoparticle formation. In some embodiments, the nanoparticles have an average diameter of about 550 nm for at least about 15 minutes after nanoparticle formation. In some embodiments, the nanoparticles have an average diameter of about 600 nm for at least about 15 minutes after nanoparticle formation. In some embodiments, the nanoparticles have an average diameter of about 650 nm for at least about 15 minutes after nanoparticle formation. In some embodiments, the nanoparticles have an average diameter of about 700 nm for at least about 15 minutes after nanoparticle formation. In some embodiments, the nanoparticles have an average diameter of about 750 nm for at least about 15 minutes after nanoparticle formation. In some embodiments, the nanoparticles have an average diameter of about 800 nm for at least about 15 minutes after nanoparticle formation. In some embodiments, the nanoparticles have an average diameter of about 850 nm for at least about 15 minutes after nanoparticle formation. In some embodiments, the nanoparticles have an average diameter of about 900 nm for at least about 15 minutes after nanoparticle formation. In some embodiments, the nanoparticles have an average diameter of about 950 nm for at least about 15 minutes after nanoparticle formation. In some embodiments, the nanoparticles have an average diameter of about 1000 nm for at least about 15 minutes after nanoparticle formation.

In some embodiments, the nanoparticles have an average diameter of about 1000 nm or less for at least about 4 hours after nanoparticle formation. In some embodiments, the nanoparticles have an average diameter of about 950 nm or less for at least about 4 hours after nanoparticle formation. In some embodiments, the nanoparticles have an average diameter of about 900 nm or less for at least about 4 hours after nanoparticle formation. In some embodiments, the nanoparticles have an average diameter of about 850 nm or less for at least about 4 hours after nanoparticle formation. In some embodiments, the nanoparticles have an average diameter of about 800 nm or less for at least about 4 hours after nanoparticle formation. In some embodiments, the nanoparticles have an average diameter of about 750 nm or less for at least about 4 hours after nanoparticle formation. In some embodiments, the nanoparticles have an average diameter of about 700 nm or less for at least about 4 hours after nanoparticle formation. In some embodiments, the nanoparticles have an average diameter of about 650 nm or less for at least about 4 hours after nanoparticle formation. In some embodiments, the nanoparticles have an average diameter of about 600 nm or less for at least about 4 hours after nanoparticle formation. In some embodiments, the nanoparticles have an average diameter of about 550 nm or less for at least about 4 hours after nanoparticle formation. In some embodiments, the nanoparticles have an average diameter of about 500 nm or less for at least about 4 hours after nanoparticle formation. In some embodiments, the nanoparticles have an average diameter of about 450 nm or less for at least about 4 hours after nanoparticle formation. In some embodiments, the nanoparticles have an average diameter of about 400 nm or less for at least about 4 hours after nanoparticle formation. In some embodiments, the nanoparticles have an average diameter of about 350 nm or less for at least about 4 hours after nanoparticle formation. In some embodiments, the nanoparticles have an average diameter of about 300 nm or less for at least about 4 hours after nanoparticle formation. In some embodiments, the nanoparticles have an average diameter of about 250 nm or less for at least about 4 hours after nanoparticle formation. In some embodiments, the nanoparticles have an average diameter of about 240 nm or less for at least about 4 hours after nanoparticle formation. In some embodiments, the nanoparticles have an average diameter of about 230 nm or less for at least about 4 hours after nanoparticle formation. In some embodiments, the nanoparticles have an average diameter of about 220 nm or less for at least about 4 hours after nanoparticle formation. In some embodiments, the nanoparticles have an average diameter of about 210 nm or less for at least about 4 hours after nanoparticle formation. In some embodiments, the nanoparticles have an average diameter of about 200 nm or less for at least about 4 hours after nanoparticle formation. In some embodiments, the nanoparticles have an average diameter of about 190 nm or less for at least about 4 hours after nanoparticle formation. In some embodiments, the nanoparticles have an average diameter of about 180 nm or less for at least about 4 hours after nanoparticle formation. In some embodiments, the nanoparticles have an average diameter of about 170 nm or less for at least about 4 hours after nanoparticle formation. In some embodiments, the nanoparticles have an average diameter of about 160 nm or less for at least about 4 hours after nanoparticle formation. In some embodiments, the nanoparticles have an average diameter of about 150 nm or less for at least about 4 hours after nanoparticle formation. In some embodiments, the nanoparticles have an average diameter of about 140 nm or less for at least about 4 hours after nanoparticle formation. In some embodiments, the nanoparticles have an average diameter of about 130 nm or less for at least about 4 hours after nanoparticle formation. In some embodiments, the nanoparticles have an average diameter of about 120 nm or less for at least about 4 hours after nanoparticle formation. In some embodiments, the nanoparticles have an average diameter of about 110 nm or less for at least about 4 hours after nanoparticle formation. In some embodiments, the nanoparticles have an average diameter of about 100 nm or less for at least about 4 hours after nanoparticle formation. In some embodiments, the nanoparticles have an average diameter of about 90 nm or less for at least about 4 hours after nanoparticle formation. In some embodiments, the nanoparticles have an average diameter of about 80 nm or less for at least about 4 hours after nanoparticle formation. In some embodiments, the nanoparticles have an average diameter of about 70 nm or less for at least about 4 hours after nanoparticle formation. In some embodiments, the nanoparticles have an average diameter of about 60 nm or less for at least about 4 hours after nanoparticle formation. In some embodiments, the nanoparticles have an average diameter of about 50 nm or less for at least about 4 hours after nanoparticle formation. In some embodiments, the nanoparticles have an average diameter of about 40 nm or less for at least about 4 hours after nanoparticle formation. In some embodiments, the nanoparticles have an average diameter of about 30 nm or less for at least about 4 hours after nanoparticle formation. In some embodiments, the nanoparticles have an average diameter of about 20 nm or less for at least about 4 hours after nanoparticle formation. In some embodiments, the nanoparticles have an average diameter of about 10 nm or less for at least about 4 hours after nanoparticle formation.

In some embodiments, the nanoparticles have an average diameter of about 10 nm or greater for at least about 4 hours after nanoparticle formation. In some embodiments, the nanoparticles have an average diameter of about 20 nm or greater for at least about 4 hours after nanoparticle formation. In some embodiments, the nanoparticles have an average diameter of about 30 nm or greater for at least about 4 hours after nanoparticle formation. In some embodiments, the nanoparticles have an average diameter of about 40 nm or greater for at least about 4 hours after nanoparticle formation. In some embodiments, the nanoparticles have an average diameter of about 50 nm or greater for at least about 4 hours after nanoparticle formation. In some embodiments, the nanoparticles have an average diameter of about 60 nm or greater for at least about 4 hours after nanoparticle formation. In some embodiments, the nanoparticles have an average diameter of about 70 nm or greater for at least about 4 hours after nanoparticle formation. In some embodiments, the nanoparticles have an average diameter of about 80 nm or greater for at least about 4 hours after nanoparticle formation. In some embodiments, the nanoparticles have an average diameter of about 90 nm or greater for at least about 4 hours after nanoparticle formation. In some embodiments, the nanoparticles have an average diameter of about 100 nm or greater for at least about 4 hours after nanoparticle formation. In some embodiments, the nanoparticles have an average diameter of about 110 nm or greater for at least about 4 hours after nanoparticle formation. In some embodiments, the nanoparticles have an average diameter of about 120 nm or greater for at least about 4 hours after nanoparticle formation. In some embodiments, the nanoparticles have an average diameter of about 130 nm or greater for at least about 4 hours after nanoparticle formation. In some embodiments, the nanoparticles have an average diameter of about 140 nm or greater for at least about 4 hours after nanoparticle formation. In some embodiments, the nanoparticles have an average diameter of about 150 nm or greater for at least about 4 hours after nanoparticle formation. In some embodiments, the nanoparticles have an average diameter of about 160 nm or greater for at least about 4 hours after nanoparticle formation. In some embodiments, the nanoparticles have an average diameter of about 170 nm or greater for at least about 4 hours after nanoparticle formation. In some embodiments, the nanoparticles have an average diameter of about 180 nm or greater for at least about 4 hours after nanoparticle formation. In some embodiments, the nanoparticles have an average diameter of about 190 nm or greater for at least about 4 hours after nanoparticle formation. In some embodiments, the nanoparticles have an average diameter of about 200 nm or greater for at least about 4 hours after nanoparticle formation. In some embodiments, the nanoparticles have an average diameter of about 210 nm or greater for at least about 4 hours after nanoparticle formation. In some embodiments, the nanoparticles have an average diameter of about 220 nm or greater for at least about 4 hours after nanoparticle formation. In some embodiments, the nanoparticles have an average diameter of about 230 nm or greater for at least about 4 hours after nanoparticle formation. In some embodiments, the nanoparticles have an average diameter of about 240 nm or greater for at least about 4 hours after nanoparticle formation. In some embodiments, the nanoparticles have an average diameter of about 250 nm or greater for at least about 4 hours after nanoparticle formation. In some embodiments, the nanoparticles have an average diameter of about 300 nm or greater for at least about 4 hours after nanoparticle formation. In some embodiments, the nanoparticles have an average diameter of about 350 nm or greater for at least about 4 hours after nanoparticle formation. In some embodiments, the nanoparticles have an average diameter of about 400 nm or greater for at least about 4 hours after nanoparticle formation. In some embodiments, the nanoparticles have an average diameter of about 450 nm or greater for at least about 4 hours after nanoparticle formation. In some embodiments, the nanoparticles have an average diameter of about 500 nm or greater for at least about 4 hours after nanoparticle formation. In some embodiments, the nanoparticles have an average diameter of about 550 nm or greater for at least about 4 hours after nanoparticle formation. In some embodiments, the nanoparticles have an average diameter of about 600 nm or greater for at least about 4 hours after nanoparticle formation. In some embodiments, the nanoparticles have an average diameter of about 650 nm or greater for at least about 4 hours after nanoparticle formation. In some embodiments, the nanoparticles have an average diameter of about 700 nm or greater for at least about 4 hours after nanoparticle formation. In some embodiments, the nanoparticles have an average diameter of about 750 nm or greater for at least about 4 hours after nanoparticle formation. In some embodiments, the nanoparticles have an average diameter of about 800 nm or greater for at least about 4 hours after nanoparticle formation. In some embodiments, the nanoparticles have an average diameter of about 850 nm or greater for at least about 4 hours after nanoparticle formation. In some embodiments, the nanoparticles have an average diameter of about 900 nm or greater for at least about 4 hours after nanoparticle formation. In some embodiments, the nanoparticles have an average diameter of about 950 nm or greater for at least about 4 hours after nanoparticle formation In some embodiments, the nanoparticles have an average diameter of from about 10 nm to about 1000 nm for at least about 4 hours after nanoparticle formation. In some embodiments, the nanoparticles have an average diameter of from about 10 nm to about 950 nm for at least about 4 hours after nanoparticle formation. In some embodiments, the nanoparticles have an average diameter of from about 10 nm to about 900 nm for at least about 4 hours after nanoparticle formation. In some embodiments, the nanoparticles have an average diameter of from about 10 nm to about 850 nm for at least about 4 hours after nanoparticle formation. In some embodiments, the nanoparticles have an average diameter of from about 10 nm to about 800 nm for at least about 4 hours after nanoparticle formation. In some embodiments, the nanoparticles have an average diameter of from about 10 nm to about 750 nm for at least about 4 hours after nanoparticle formation. In some embodiments, the nanoparticles have an average diameter of from about 10 nm to about 700 nm for at least about 4 hours after nanoparticle formation. In some embodiments, the nanoparticles have an average diameter of from about 10 nm to about 650 nm for at least about 4 hours after nanoparticle formation. In some embodiments, the nanoparticles have an average diameter of from about 10 nm to about 600 nm for at least about 4 hours after nanoparticle formation. In some embodiments, the nanoparticles have an average diameter of from about 10 nm to about 550 nm for at least about 4 hours after nanoparticle formation for at least about 4 hours after nanoparticle formation. In some embodiments, the nanoparticles have an average diameter of from about 10 nm to about 500 nm for at least about 4 hours after nanoparticle formation. In some embodiments, the nanoparticles have an average diameter of from about 10 nm to about 450 nm for at least about 4 hours after nanoparticle formation. In some embodiments, the nanoparticles have an average diameter of from about 10 nm to about 400 nm for at least about 4 hours after nanoparticle formation. In some embodiments, the nanoparticles have an average diameter of from about 10 nm to about 350 nm for at least about 4 hours after nanoparticle formation. In some embodiments, the nanoparticles have an average diameter of from about 10 nm to about 300 nm for at least about 4 hours after nanoparticle formation. In some embodiments, the nanoparticles have an average diameter of from about 10 nm to about 250 nm for at least about 4 hours after nanoparticle formation. In some embodiments, the nanoparticles have an average diameter of from about 10 nm to about 240 nm for at least about 4 hours after nanoparticle formation. In some embodiments, the nanoparticles have an average diameter of from about 10 nm to about 230 nm for at least about 4 hours after nanoparticle formation. In some embodiments, the nanoparticles have an average diameter of from about 10 nm to about 220 nm for at least about 4 hours after nanoparticle formation. In some embodiments, the nanoparticles have an average diameter of from about 10 nm to about 210 nm for at least about 4 hours after nanoparticle formation. In some embodiments, the nanoparticles have an average diameter of from about 10 nm to about 200 nm for at least about 4 hours after nanoparticle formation. In some embodiments, the nanoparticles have an average diameter of from about 10 nm to about 190 nm for at least about 4 hours after nanoparticle formation. In some embodiments, the nanoparticles have an average diameter of from about 10 nm to about 180 nm for at least about 4 hours after nanoparticle formation. In some embodiments, the nanoparticles have an average diameter of from about 10 nm to about 170 nm for at least about 4 hours after nanoparticle formation. In some embodiments, the nanoparticles have an average diameter of from about 10 nm to about 160 nm for at least about 4 hours after nanoparticle formation. In some embodiments, the nanoparticles have an average diameter of from about 10 nm to about 150 nm for at least about 4 hours after nanoparticle formation. In some embodiments, the nanoparticles have an average diameter of from about 10 nm to about 140 nm for at least about 4 hours after nanoparticle formation. In some embodiments, the nanoparticles have an average diameter of from about 10 nm to about 130 nm for at least about 4 hours after nanoparticle formation. In some embodiments, the nanoparticles have an average diameter of from about 10 nm to about 120 nm for at least about 4 hours after nanoparticle formation. In some embodiments, the nanoparticles have an average diameter of from about 10 nm to about 110 nm for at least about 4 hours after nanoparticle formation. In some embodiments, the nanoparticles have an average diameter of from about 10 nm to about 100 nm for at least about 4 hours after nanoparticle formation. In some embodiments, the nanoparticles have an average diameter of from about 10 nm to about 90 nm for at least about 4 hours after nanoparticle formation. In some embodiments, the nanoparticles have an average diameter of from about 10 nm to about 80 nm for at least about 4 hours after nanoparticle formation. In some embodiments, the nanoparticles have an average diameter of from about 10 nm to about 70 nm for at least about 4 hours after nanoparticle formation. In some embodiments, the nanoparticles have an average diameter of from about 10 nm to about 60 nm for at least about 4 hours after nanoparticle formation. In some embodiments, the nanoparticles have an average diameter of from about 10 nm to about 50 nm for at least about 4 hours after nanoparticle formation. In some embodiments, the nanoparticles have an average diameter of from about 10 nm to about 40 nm for at least about 4 hours after nanoparticle formation. In some embodiments, the nanoparticles have an average diameter of from about 10 nm to about 30 nm for at least about 4 hours after nanoparticle formation. In some embodiments, the nanoparticles have an average diameter of from about 10 nm to about 20 nm for at least about 4 hours after nanoparticle formation.

In some embodiments, the nanoparticles have an average diameter of about 10 nm for at least about 4 hours after nanoparticle formation. In some embodiments, the nanoparticles have an average diameter of about 20 nm for at least about 4 hours after nanoparticle formation. In some embodiments, the nanoparticles have an average diameter of about 30 nm for at least about 4 hours after nanoparticle formation. In some embodiments, the nanoparticles have an average diameter of about 40 nm for at least about 4 hours after nanoparticle formation. In some embodiments, the nanoparticles have an average diameter of about 50 nm for at least about 4 hours after nanoparticle formation. In some embodiments, the nanoparticles have an average diameter of about 60 nm for at least about 4 hours after nanoparticle formation. In some embodiments, the nanoparticles have an average diameter of about 70 nm for at least about 4 hours after nanoparticle formation. In some embodiments, the nanoparticles have an average diameter of about 80 nm for at least about 4 hours after nanoparticle formation. In some embodiments, the nanoparticles have an average diameter of about 90 nm for at least about 4 hours after nanoparticle formation. In some embodiments, the nanoparticles have an average diameter of about 100 nm for at least about 4 hours after nanoparticle formation. In some embodiments, the nanoparticles have an average diameter of about 110 nm for at least about 4 hours after nanoparticle formation. In some embodiments, the nanoparticles have an average diameter of about 120 nm for at least about 4 hours after nanoparticle formation. In some embodiments, the nanoparticles have an average diameter of about 130 nm for at least about 4 hours after nanoparticle formation. In some embodiments, the nanoparticles have an average diameter of about 140 nm for at least about 4 hours after nanoparticle formation. In some embodiments, the nanoparticles have an average diameter of about 150 nm for at least about 4 hours after nanoparticle formation. In some embodiments, the nanoparticles have an average diameter of about 160 nm for at least about 4 hours after nanoparticle formation. In some embodiments, the nanoparticles have an average diameter of about 170 nm for at least about 4 hours after nanoparticle formation. In some embodiments, the nanoparticles have an average diameter of about 180 nm for at least about 4 hours after nanoparticle formation. In some embodiments, the nanoparticles have an average diameter of about 190 nm for at least about 4 hours after nanoparticle formation. In some embodiments, the nanoparticles have an average diameter of about 200 nm for at least about 4 hours after nanoparticle formation. In some embodiments, the nanoparticles have an average diameter of about 210 nm for at least about 4 hours after nanoparticle formation. In some embodiments, the nanoparticles have an average diameter of about 220 nm for at least about 4 hours after nanoparticle formation. In some embodiments, the nanoparticles have an average diameter of about 230 nm for at least about 4 hours after nanoparticle formation. In some embodiments, the nanoparticles have an average diameter of about 240 nm for at least about 4 hours after nanoparticle formation. In some embodiments, the nanoparticles have an average diameter of about 250 nm for at least about 4 hours after nanoparticle formation. In some embodiments, the nanoparticles have an average diameter of about 300 nm for at least about 4 hours after nanoparticle formation. In some embodiments, the nanoparticles have an average diameter of about 350 nm for at least about 4 hours after nanoparticle formation. In some embodiments, the nanoparticles have an average diameter of about 400 nm for at least about 4 hours after nanoparticle formation. In some embodiments, the nanoparticles have an average diameter of about 450 nm for at least about 4 hours after nanoparticle formation. In some embodiments, the nanoparticles have an average diameter of about 500 nm for at least about 4 hours after nanoparticle formation. In some embodiments, the nanoparticles have an average diameter of about 550 nm for at least about 4 hours after nanoparticle formation. In some embodiments, the nanoparticles have an average diameter of about 600 nm for at least about 4 hours after nanoparticle formation. In some embodiments, the nanoparticles have an average diameter of about 650 nm for at least about 4 hours after nanoparticle formation. In some embodiments, the nanoparticles have an average diameter of about 700 nm for at least about 4 hours after nanoparticle formation. In some embodiments, the nanoparticles have an average diameter of about 750 nm for at least about 4 hours after nanoparticle formation. In some embodiments, the nanoparticles have an average diameter of about 800 nm for at least about 4 hours after nanoparticle formation. In some embodiments, the nanoparticles have an average diameter of about 850 nm for at least about 4 hours after nanoparticle formation. In some embodiments, the nanoparticles have an average diameter of about 900 nm for at least about 4 hours after nanoparticle formation. In some embodiments, the nanoparticles have an average diameter of about 950 nm for at least about 4 hours after nanoparticle formation. In some embodiments, the nanoparticles have an average diameter of about 1000 nm for at least about 4 hours after nanoparticle formation.

In some embodiments, the nanoparticles have an average diameter of from about 10 nm to about 1000 nm. In some embodiments, the nanoparticles have an average diameter of from about 10 nm to about 950 nm. In some embodiments, the nanoparticles have an average diameter of from about 10 nm to about 900 nm. In some embodiments, the nanoparticles have an average diameter of from about 10 nm to about 850 nm. In some embodiments, the nanoparticles have an average diameter of from about 10 nm to about 800 nm. In some embodiments, the nanoparticles have an average diameter of from about 10 nm to about 750 nm. In some embodiments, the nanoparticles have an average diameter of from about 10 nm to about 700 nm. In some embodiments, the nanoparticles have an average diameter of from about 10 nm to about 650 nm. In some embodiments, the nanoparticles have an average diameter of from about 10 nm to about 600 nm. In some embodiments, the nanoparticles have an average diameter of from about 10 nm to about 550 nm. In some embodiments, the nanoparticles have an average diameter of from about 10 nm to about 500 nm. In some embodiments, the nanoparticles have an average diameter of from about 10 nm to about 450 nm. In some embodiments, the nanoparticles have an average diameter of from about 10 nm to about 400 nm. In some embodiments, the nanoparticles have an average diameter of from about 10 nm to about 350 nm. In some embodiments, the nanoparticles have an average diameter of from about 10 nm to about 300 nm. In some embodiments, the nanoparticles have an average diameter of from about 10 nm to about 250 nm. In some embodiments, the nanoparticles have an average diameter of from about 10 nm to about 240 nm. In some embodiments, the nanoparticles have an average diameter of from about 10 nm to about 230 nm. In some embodiments, the nanoparticles have an average diameter of from about 10 nm to about 220 nm. In some embodiments, the nanoparticles have an average diameter of from about 10 nm to about 210 nm. In some embodiments, the nanoparticles have an average diameter of from about 10 nm to about 200 nm. In some embodiments, the nanoparticles have an average diameter of from about 10 nm to about 190 nm. In some embodiments, the nanoparticles have an average diameter of from about 10 nm to about 180 nm. In some embodiments, the nanoparticles have an average diameter of from about 10 nm to about 170 nm. In some embodiments, the nanoparticles have an average diameter of from about 10 nm to about 160 nm. In some embodiments, the nanoparticles have an average diameter of from about 10 nm to about 150 nm. In some embodiments, the nanoparticles have an average diameter of from about 10 nm to about 140 nm. In some embodiments, the nanoparticles have an average diameter of from about 10 nm to about 130 nm. In some embodiments, the nanoparticles have an average diameter of from about 10 nm to about 120 nm. In some embodiments, the nanoparticles have an average diameter of from about 10 nm to about 110 nm. In some embodiments, the nanoparticles have an average diameter of from about 10 nm to about 100 nm. In some embodiments, the nanoparticles have an average diameter of from about 10 nm to about 90 nm. In some embodiments, the nanoparticles have an average diameter of from about 10 nm to about 80 nm. In some embodiments, the nanoparticles have an average diameter of from about 10 nm to about 70 nm. In some embodiments, the nanoparticles have an average diameter of from about 10 nm to about 60 nm. In some embodiments, the nanoparticles have an average diameter of from about 10 nm to about 50 nm. In some embodiments, the nanoparticles have an average diameter of from about 10 nm to about 40 nm. In some embodiments, the nanoparticles have an average diameter of from about 10 nm to about 30 nm. In some embodiments, the nanoparticles have an average diameter of from about 10 nm to about 20 nm.

In some embodiments, the nanoparticles have an average diameter of from about 20 nm to about 1000 nm. In some embodiments, the nanoparticles have an average diameter of from about 20 nm to about 950 nm. In some embodiments, the nanoparticles have an average diameter of from about 20 nm to about 900 nm. In some embodiments, the nanoparticles have an average diameter of from about 20 nm to about 850 nm. In some embodiments, the nanoparticles have an average diameter of from about 20 nm to about 800 nm. In some embodiments, the nanoparticles have an average diameter of from about 20 nm to about 750 nm. In some embodiments, the nanoparticles have an average diameter of from about 20 nm to about 700 nm. In some embodiments, the nanoparticles have an average diameter of from about 20 nm to about 650 nm. In some embodiments, the nanoparticles have an average diameter of from about 20 nm to about 600 nm. In some embodiments, the nanoparticles have an average diameter of from about 20 nm to about 550 nm. In some embodiments, the nanoparticles have an average diameter of from about 20 nm to about 500 nm. In some embodiments, the nanoparticles have an average diameter of from about 20 nm to about 450 nm. In some embodiments, the nanoparticles have an average diameter of from about 20 nm to about 400 nm. In some embodiments, the nanoparticles have an average diameter of from about 20 nm to about 350 nm. In some embodiments, the nanoparticles have an average diameter of from about 20 nm to about 300 nm. In some embodiments, the nanoparticles have an average diameter of from about 20 nm to about 250 nm. In some embodiments, the nanoparticles have an average diameter of from about 20 nm to about 240 nm. In some embodiments, the nanoparticles have an average diameter of from about 20 nm to about 230 nm. In some embodiments, the nanoparticles have an average diameter of from about 20 nm to about 220 nm. In some embodiments, the nanoparticles have an average diameter of from about 20 nm to about 210 nm. In some embodiments, the nanoparticles have an average diameter of from about 20 nm to about 200 nm. In some embodiments, the nanoparticles have an average diameter of from about 20 nm to about 190 nm. In some embodiments, the nanoparticles have an average diameter of from about 20 nm to about 180 nm. In some embodiments, the nanoparticles have an average diameter of from about 20 nm to about 170 nm. In some embodiments, the nanoparticles have an average diameter of from about 20 nm to about 160 nm. In some embodiments, the nanoparticles have an average diameter of from about 20 nm to about 150 nm. In some embodiments, the nanoparticles have an average diameter of from about 20 nm to about 140 nm. In some embodiments, the nanoparticles have an average diameter of from about 20 nm to about 130 nm. In some embodiments, the nanoparticles have an average diameter of from about 20 nm to about 120 nm. In some embodiments, the nanoparticles have an average diameter of from about 20 nm to about 110 nm. In some embodiments, the nanoparticles have an average diameter of from about 20 nm to about 100 nm. In some embodiments, the nanoparticles have an average diameter of from about 20 nm to about 90 nm. In some embodiments, the nanoparticles have an average diameter of from about 20 nm to about 80 nm. In some embodiments, the nanoparticles have an average diameter of from about 20 nm to about 70 nm. In some embodiments, the nanoparticles have an average diameter of from about 20 nm to about 60 nm. In some embodiments, the nanoparticles have an average diameter of from about 20 nm to about 50 nm. In some embodiments, the nanoparticles have an average diameter of from about 20 nm to about 40 nm. In some embodiments, the nanoparticles have an average diameter of from about 20 nm to about 30 nm.

In some embodiments, the nanoparticles have an average diameter of from about 30 nm to about 1000 nm. In some embodiments, the nanoparticles have an average diameter of from about 30 nm to about 950 nm. In some embodiments, the nanoparticles have an average diameter of from about 30 nm to about 900 nm. In some embodiments, the nanoparticles have an average diameter of from about 30 nm to about 850 nm. In some embodiments, the nanoparticles have an average diameter of from about 30 nm to about 800 nm. In some embodiments, the nanoparticles have an average diameter of from about 30 nm to about 750 nm. In some embodiments, the nanoparticles have an average diameter of from about 30 nm to about 700 nm. In some embodiments, the nanoparticles have an average diameter of from about 30 nm to about 650 nm. In some embodiments, the nanoparticles have an average diameter of from about 30 nm to about 600 nm. In some embodiments, the nanoparticles have an average diameter of from about 30 nm to about 550 nm. In some embodiments, the nanoparticles have an average diameter of from about 30 nm to about 500 nm. In some embodiments, the nanoparticles have an average diameter of from about 30 nm to about 450 nm. In some embodiments, the nanoparticles have an average diameter of from about 30 nm to about 400 nm. In some embodiments, the nanoparticles have an average diameter of from about 30 nm to about 350 nm. In some embodiments, the nanoparticles have an average diameter of from about 30 nm to about 300 nm. In some embodiments, the nanoparticles have an average diameter of from about 30 nm to about 250 nm. In some embodiments, the nanoparticles have an average diameter of from about 30 nm to about 240 nm. In some embodiments, the nanoparticles have an average diameter of from about 30 nm to about 230 nm. In some embodiments, the nanoparticles have an average diameter of from about 30 nm to about 220 nm. In some embodiments, the nanoparticles have an average diameter of from about 30 nm to about 210 nm. In some embodiments, the nanoparticles have an average diameter of from about 30 nm to about 200 nm. In some embodiments, the nanoparticles have an average diameter of from about 30 nm to about 190 nm. In some embodiments, the nanoparticles have an average diameter of from about 30 nm to about 180 nm. In some embodiments, the nanoparticles have an average diameter of from about 30 nm to about 170 nm. In some embodiments, the nanoparticles have an average diameter of from about 30 nm to about 160 nm. In some embodiments, the nanoparticles have an average diameter of from about 30 nm to about 150 nm. In some embodiments, the nanoparticles have an average diameter of from about 30 nm to about 140 nm. In some embodiments, the nanoparticles have an average diameter of from about 30 nm to about 130 nm. In some embodiments, the nanoparticles have an average diameter of from about 30 nm to about 120 nm. In some embodiments, the nanoparticles have an average diameter of from about 30 nm to about 110 nm. In some embodiments, the nanoparticles have an average diameter of from about 30 nm to about 100 nm. In some embodiments, the nanoparticles have an average diameter of from about 30 nm to about 90 nm. In some embodiments, the nanoparticles have an average diameter of from about 30 nm to about 80 nm. In some embodiments, the nanoparticles have an average diameter of from about 30 nm to about 70 nm. In some embodiments, the nanoparticles have an average diameter of from about 30 nm to about 60 nm. In some embodiments, the nanoparticles have an average diameter of from about 30 nm to about 50 nm. In some embodiments, the nanoparticles have an average diameter of from about 30 nm to about 40 nm. In some embodiments, the nanoparticles have an average diameter of from about 30 nm to about 40 nm.

In some embodiments, the nanoparticles have an average diameter of from about 40 nm to about 1000 nm. In some embodiments, the nanoparticles have an average diameter of from about 40 nm to about 950 nm. In some embodiments, the nanoparticles have an average diameter of from about 40 nm to about 900 nm. In some embodiments, the nanoparticles have an average diameter of from about 40 nm to about 850 nm. In some embodiments, the nanoparticles have an average diameter of from about 40 nm to about 800 nm. In some embodiments, the nanoparticles have an average diameter of from about 40 nm to about 750 nm. In some embodiments, the nanoparticles have an average diameter of from about 40 nm to about 700 nm. In some embodiments, the nanoparticles have an average diameter of from about 40 nm to about 650 nm. In some embodiments, the nanoparticles have an average diameter of from about 40 nm to about 600 nm. In some embodiments, the nanoparticles have an average diameter of from about 40 nm to about 550 nm. In some embodiments, the nanoparticles have an average diameter of from about 40 nm to about 500 nm. In some embodiments, the nanoparticles have an average diameter of from about 40 nm to about 450 nm. In some embodiments, the nanoparticles have an average diameter of from about 40 nm to about 400 nm. In some embodiments, the nanoparticles have an average diameter of from about 40 nm to about 350 nm. In some embodiments, the nanoparticles have an average diameter of from about 40 nm to about 300 nm. In some embodiments, the nanoparticles have an average diameter of from about 40 nm to about 250 nm. In some embodiments, the nanoparticles have an average diameter of from about 40 nm to about 240 nm. In some embodiments, the nanoparticles have an average diameter of from about 40 nm to about 230 nm. In some embodiments, the nanoparticles have an average diameter of from about 40 nm to about 220 nm. In some embodiments, the nanoparticles have an average diameter of from about 40 nm to about 210 nm. In some embodiments, the nanoparticles have an average diameter of from about 40 nm to about 200 nm. In some embodiments, the nanoparticles have an average diameter of from about 40 nm to about 190 nm. In some embodiments, the nanoparticles have an average diameter of from about 40 nm to about 180 nm. In some embodiments, the nanoparticles have an average diameter of from about 40 nm to about 170 nm. In some embodiments, the nanoparticles have an average diameter of from about 40 nm to about 160 nm. In some embodiments, the nanoparticles have an average diameter of from about 40 nm to about 150 nm. In some embodiments, the nanoparticles have an average diameter of from about 40 nm to about 140 nm. In some embodiments, the nanoparticles have an average diameter of from about 40 nm to about 130 nm. In some embodiments, the nanoparticles have an average diameter of from about 40 nm to about 120 nm. In some embodiments, the nanoparticles have an average diameter of from about 40 nm to about 110 nm. In some embodiments, the nanoparticles have an average diameter of from about 40 nm to about 100 nm. In some embodiments, the nanoparticles have an average diameter of from about 40 nm to about 90 nm. In some embodiments, the nanoparticles have an average diameter of from about 40 nm to about 80 nm. In some embodiments, the nanoparticles have an average diameter of from about 40 nm to about 70 nm. In some embodiments, the nanoparticles have an average diameter of from about 40 nm to about 60 nm. In some embodiments, the nanoparticles have an average diameter of from about 40 nm to about 50 nm.

In some embodiments, the nanoparticles have an average diameter of from about 50 nm to about 1000 nm. In some embodiments, the nanoparticles have an average diameter of from about 50 nm to about 950 nm. In some embodiments, the nanoparticles have an average diameter of from about 50 nm to about 900 nm. In some embodiments, the nanoparticles have an average diameter of from about 50 nm to about 850 nm. In some embodiments, the nanoparticles have an average diameter of from about 50 nm to about 800 nm. In some embodiments, the nanoparticles have an average diameter of from about 50 nm to about 750 nm. In some embodiments, the nanoparticles have an average diameter of from about 50 nm to about 700 nm. In some embodiments, the nanoparticles have an average diameter of from about 50 nm to about 650 nm. In some embodiments, the nanoparticles have an average diameter of from about 50 nm to about 600 nm. In some embodiments, the nanoparticles have an average diameter of from about 50 nm to about 550 nm. In some embodiments, the nanoparticles have an average diameter of from about 50 nm to about 500 nm. In some embodiments, the nanoparticles have an average diameter of from about 50 nm to about 450 nm. In some embodiments, the nanoparticles have an average diameter of from about 50 nm to about 400 nm. In some embodiments, the nanoparticles have an average diameter of from about 50 nm to about 350 nm. In some embodiments, the nanoparticles have an average diameter of from about 50 nm to about 300 nm. In some embodiments, the nanoparticles have an average diameter of from about 50 nm to about 250 nm. In some embodiments, the nanoparticles have an average diameter of from about 50 nm to about 240 nm. In some embodiments, the nanoparticles have an average diameter of from about 50 nm to about 230 nm. In some embodiments, the nanoparticles have an average diameter of from about 50 nm to about 220 nm. In some embodiments, the nanoparticles have an average diameter of from about 50 nm to about 210 nm. In some embodiments, the nanoparticles have an average diameter of from about 50 nm to about 200 nm. In some embodiments, the nanoparticles have an average diameter of from about 50 nm to about 190 nm. In some embodiments, the nanoparticles have an average diameter of from about 50 nm to about 180 nm. In some embodiments, the nanoparticles have an average diameter of from about 50 nm to about 170 nm. In some embodiments, the nanoparticles have an average diameter of from about 50 nm to about 160 nm. In some embodiments, the nanoparticles have an average diameter of from about 50 nm to about 150 nm. In some embodiments, the nanoparticles have an average diameter of from about 50 nm to about 140 nm. In some embodiments, the nanoparticles have an average diameter of from about 50 nm to about 130 nm. In some embodiments, the nanoparticles have an average diameter of from about 50 nm to about 120 nm. In some embodiments, the nanoparticles have an average diameter of from about 50 nm to about 110 nm. In some embodiments, the nanoparticles have an average diameter of from about 50 nm to about 100 nm. In some embodiments, the nanoparticles have an average diameter of from about 50 nm to about 90 nm. In some embodiments, the nanoparticles have an average diameter of from about 50 nm to about 80 nm. In some embodiments, the nanoparticles have an average diameter of from about 50 nm to about 70 nm. In some embodiments, the nanoparticles have an average diameter of from about 50 nm to about 60 nm.

In some embodiments, the nanoparticles have an average diameter of about 10 nm. In some embodiments, the nanoparticles have an average diameter of about 20 nm. In some embodiments, the nanoparticles have an average diameter of about 30 nm. In some embodiments, the nanoparticles have an average diameter of about 40 nm. In some embodiments, the nanoparticles have an average diameter of about 50 nm. In some embodiments, the nanoparticles have an average diameter of about 60 nm. In some embodiments, the nanoparticles have an average diameter of about 70 nm. In some embodiments, the nanoparticles have an average diameter of about 80 nm. In some embodiments, the nanoparticles have an average diameter of about 90 nm. In some embodiments, the nanoparticles have an average diameter of about 100 nm. In some embodiments, the nanoparticles have an average diameter of about 110 nm. In some embodiments, the nanoparticles have an average diameter of about 120 nm. In some embodiments, the nanoparticles have an average diameter of about 130 nm. In some embodiments, the nanoparticles have an average diameter of about 140 nm. In some embodiments, the nanoparticles have an average diameter of about 150 nm. In some embodiments, the nanoparticles have an average diameter of about 160 nm. In some embodiments, the nanoparticles have an average diameter of about 170 nm. In some embodiments, the nanoparticles have an average diameter of about 180 nm. In some embodiments, the nanoparticles have an average diameter of about 190 nm. In some embodiments, the nanoparticles have an average diameter of about 200 nm. In some embodiments, the nanoparticles have an average diameter of about 210 nm. In some embodiments, the nanoparticles have an average diameter of about 220 nm. In some embodiments, the nanoparticles have an average diameter of about 230 nm. In some embodiments, the nanoparticles have an average diameter of about 240 nm. In some embodiments, the nanoparticles have an average diameter of about 250 nm. In some embodiments, the nanoparticles have an average diameter of about 300 nm. In some embodiments, the nanoparticles have an average diameter of about 350 nm. In some embodiments, the nanoparticles have an average diameter of about 400 nm. In some embodiments, the nanoparticles have an average diameter of about 450 nm. In some embodiments, the nanoparticles have an average diameter of about 500 nm. In some embodiments, the nanoparticles have an average diameter of about 550 nm. In some embodiments, the nanoparticles have an average diameter of about 600 nm. In some embodiments, the nanoparticles have an average diameter of about 650 nm. In some embodiments, the nanoparticles have an average diameter of about 700 nm. In some embodiments, the nanoparticles have an average diameter of about 750 nm. In some embodiments, the nanoparticles have an average diameter of about 800 nm. In some embodiments, the nanoparticles have an average diameter of about 850 nm. In some embodiments, the nanoparticles have an average diameter of about 900 nm. In some embodiments, the nanoparticles have an average diameter of about 950 nm. In some embodiments, the nanoparticles have an average diameter of about 1000 nm.

In some embodiments, the composition is sterile filterable. In some embodiments, the nanoparticles have an average diameter of about 250 nm or less. In some embodiments, the nanoparticles have an average diameter of about 240 nm or less. In some embodiments, the nanoparticles have an average diameter of about 230 nm or less. In some embodiments, the nanoparticles have an average diameter of about 220 nm or less. In some embodiments, the nanoparticles have an average diameter of about 210 nm or less. In some embodiments, the nanoparticles have an average diameter of about 200 nm or less. In some embodiments, the nanoparticles have an average diameter of from about 10 nm to about 250 nm. In some embodiments, the nanoparticles have an average diameter of from about 10 nm to about 240 nm. In some embodiments, the nanoparticles have an average diameter of from about 10 nm to about 230 nm. In some embodiments, the nanoparticles have an average diameter of from about 10 nm to about 220 nm. In some embodiments, the nanoparticles have an average diameter of from about 10 nm to about 210 nm. In some embodiments, the nanoparticles have an average diameter of from about 10 nm to about 200 nm.

In some embodiments, the nanoparticles are suspended, dissolved, or emulsified in a liquid.

In some embodiments, the nanoparticles are suspended in a liquid. In some embodiments, the nanoparticles are dissolved in a liquid. In some embodiments, the nanoparticles are emulsified in a liquid.

In some embodiments, the nanoparticles are cross-linked using glutaraldehyde, glucose, or UV irradiation.

Dehydrated Composition

In some embodiments, the composition is dehydrated. In some embodiments, the composition is a lyophilized composition. In some embodiments, the dehydrated composition comprises less than about 10%, about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.05%, or about 0.01% by weight of water. In some embodiments, the dehydrated composition comprises less than about 5%, about 4%, about 3%, about 2%, about 1%, about 0.9%, about 0.8%, about 0.7%, about 0.6%, about 0.5%, about 0.4%, about 0.3%, about 0.2%, about 0.1%, about 0.05%, or about 0.01% by weight of water.

In some embodiments, when the composition is dehydrated composition, such as a lyophilized composition, the composition comprises from about 0.1% to about 99% by weight of the compound. In some embodiments, the composition comprises from about 0.1% to about 75% by weight of the compound. In some embodiments, the composition comprises from about 0.1% to about 50% by weight of the compound. In some embodiments, the composition comprises from about 0.1% to about 25% by weight of the compound. In some embodiments, the composition comprises from about 0.1% to about 20% by weight of the compound. In some embodiments, the composition comprises from about 0.1% to about 15% by weight of the compound. In some embodiments, the composition comprises from about 0.1% to about 10/by weight of the compound.

In some embodiments, when the composition is dehydrated composition, such as a lyophilized composition, the composition comprises from about 0.5% to about 99% by weight of the compound. In some embodiments, the composition comprises from about 0.5% to about 75% by weight of the compound. In some embodiments, the composition comprises from about 0.5% to about 50% by weight of the compound. In some embodiments, the composition comprises from about 0.5% to about 25% by weight of the compound. In some embodiments, the composition comprises from about 0.5% to about 20% by weight of the compound. In some embodiments, the composition comprises from about 0.5% to about 15% by weight of the compound. In some embodiments, the composition comprises from about 0.5% to about 10% by weight of the compound.

In some embodiments, when the composition is dehydrated composition, such as a lyophilized composition, the composition comprises from about 0.9% to about 24% by weight of the compound. In some embodiments, the composition comprises from about 1.8% to about 16% by weight of the compound.

In some embodiments, when the composition is dehydrated composition, such as a lyophilized composition, the composition comprises about 0.1%, about 0.2%, about 0.3%, about 0.4%, about 0.5%, about 0.6%, about 0.7%, about 0.8%, about 0.9%, about 1%, about 1. %, about 1.2%, about 1.3%, about 1.4%, about 1.5%, about 1.6%, about 1.7%, about 1.8%, about 1.9% about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39/%, about 40%, about 41%, about 42%, about 43%, about 44%, about 45%, about 46%, about 47%, about 48%, about 49%, or about 50% by weight of the compound. In some embodiments, the composition comprises about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9% about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, or about 25% by weight of the compound. In some embodiments, the composition comprises about 0.9%, about 1%, about 1.1%, about 1.2%, about 1.3%, about 1.4%, about 1.5%, about 1.6%, about 1.7%, about 1.8%, about 1.9% about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, or about 24% by weight of the compound. In some embodiments, the composition comprises about 1.8%, about 1.9% about 2%, about 2.5%, about 3%, about 3.5%, about 4%, about 4.5%, about 5%, about 6%, about 7%, about 8%, about 9%, about 10%, about 11%, about 12%, about 13%, about 14%, about 15%, or about 16% by weight of the compound.

In some embodiments, when the composition is dehydrated composition, such as a lyophilized composition, the composition comprises from about 50% to about 99% by weight of the pharmaceutically acceptable carrier. In some embodiments, the composition comprises from about 55% to about 99% by weight of the pharmaceutically acceptable carrier. In some embodiments, the composition comprises from about 60% to about 99% by weight of the pharmaceutically acceptable carrier. In some embodiments, the composition comprises from about 65% to about 99% by weight of the pharmaceutically acceptable carrier. In some embodiments, the composition comprises from about 70% to about 99% by weight of the pharmaceutically acceptable carrier. In some embodiments, the composition comprises from about 75% to about 99% by weight of the pharmaceutically acceptable carrier. In some embodiments, the composition comprises from about 80% to about 99% by weight of the pharmaceutically acceptable carrier. In some embodiments, the composition comprises from about 85% to about 99% by weight of the pharmaceutically acceptable carrier. In some embodiments, the composition comprises from about 90% to about 99% by weight of the pharmaceutically acceptable carrier.

In some embodiments, when the composition is dehydrated composition, such as a lyophilized composition, the composition comprises from about 76% to about 99% by weight of the pharmaceutically acceptable carrier. In some embodiments, the composition comprises from about 84% to about 98% by weight of the pharmaceutically acceptable carrier.

In some embodiments, when the composition is dehydrated composition, such as a lyophilized composition, the composition comprises about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% by weight of the pharmaceutically acceptable carrier. In some embodiments, the composition comprises about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% by weight of the pharmaceutically acceptable carrier. In some embodiments, the composition comprises about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% by weight of the pharmaceutically acceptable carrier.

Reconstitution

In some embodiments, the composition is reconstituted with an appropriate biocompatible liquid to provide a reconstituted composition. In some embodiments, appropriate biocompatible liquid is a buffered solution. Examples of suitable buffered solutions include, but are not limited to, buffered solutions of amino acids, buffered solutions of proteins, buffered solutions of sugars, buffered solutions of vitamins, buffered solutions of synthetic polymers, buffered solutions of salts (such as buffered saline or buffered aqueous media), any similar buffered solutions, or any suitable combination thereof. In some embodiments, the appropriate biocompatible liquid is a solution comprising dextrose. In some embodiments, the appropriate biocompatible liquid is a solution comprising one or more salts. In some embodiments, the appropriate biocompatible liquid is a solution suitable for intravenous use. Examples of solutions that are suitable for intravenous use, include, but are not limited to, balanced solutions, which are different solutions with different electrolyte compositions that are close to plasma composition. Such electrolyte compositions comprise crystalloids or colloids. Examples of suitable appropriate biocompatible liquids include, but are not limited to, sterile water, saline, phosphate-buffered saline, 5% dextrose in water solution, Ringer's solution, or Ringer's lactate solution. In some embodiments, the appropriate biocompatible liquid is sterile water, saline, phosphate-buffered saline, 5% dextrose in water solution, Ringer's solution, or Ringer's lactate solution. In some embodiments, the appropriate biocompatible liquid is sterile water. In some embodiments, the appropriate biocompatible liquid is saline. In some embodiments, the appropriate biocompatible liquid is phosphate-buffered saline. In some embodiments, the appropriate biocompatible liquid is 5% dextrose in water solution. In some embodiments, the appropriate biocompatible liquid is Ringer's solution. In some embodiments, the appropriate biocompatible liquid is Ringer's lactate solution. In some embodiments, the appropriate biocompatible liquid is a balanced solution, or a solution with an electrolyte composition that resembles plasma.

In some embodiments, the nanoparticles have an average diameter of from about 10 nm to about 1000 nm after reconstitution. In some embodiments, the nanoparticles have an average diameter of from about 10 nm to about 950 nm after reconstitution. In some embodiments, the nanoparticles have an average diameter of from about 10 nm to about 900 nm after reconstitution. In some embodiments, the nanoparticles have an average diameter of from about 10 nm to about 850 nm after reconstitution. In some embodiments, the nanoparticles have an average diameter of from about 10 nm to about 800 nm after reconstitution. In some embodiments, the nanoparticles have an average diameter of from about 10 nm to about 750 nm after reconstitution. In some embodiments, the nanoparticles have an average diameter of from about 10 nm to about 700 nm after reconstitution. In some embodiments, the nanoparticles have an average diameter of from about 10 nm to about 650 nm after reconstitution. In some embodiments, the nanoparticles have an average diameter of from about 10 nm to about 600 nm after reconstitution. In some embodiments, the nanoparticles have an average diameter of from about 10 nm to about 550 nm after reconstitution. In some embodiments, the nanoparticles have an average diameter of from about 10 nm to about 500 nm after reconstitution. In some embodiments, the nanoparticles have an average diameter of from about 10 nm to about 450 nm after reconstitution. In some embodiments, the nanoparticles have an average diameter of from about 10 nm to about 400 nm after reconstitution. In some embodiments, the nanoparticles have an average diameter of from about 10 nm to about 350 nm after reconstitution. In some embodiments, the nanoparticles have an average diameter of from about 10 nm to about 300 nm after reconstitution. In some embodiments, the nanoparticles have an average diameter of from about 10 nm to about 250 nm after reconstitution. In some embodiments, the nanoparticles have an average diameter of from about 10 nm to about 240 nm after reconstitution. In some embodiments, the nanoparticles have an average diameter of from about 10 nm to about 230 nm after reconstitution. In some embodiments, the nanoparticles have an average diameter of from about 10 nm to about 220 nm after reconstitution. In some embodiments, the nanoparticles have an average diameter of from about 10 nm to about 210 nm after reconstitution. In some embodiments, the nanoparticles have an average diameter of from about 10 nm to about 200 nm after reconstitution. In some embodiments, the nanoparticles have an average diameter of from about 10 nm to about 190 nm after reconstitution. In some embodiments, the nanoparticles have an average diameter of from about 10 nm to about 180 nm after reconstitution. In some embodiments, the nanoparticles have an average diameter of from about 10 nm to about 170 nm after reconstitution. In some embodiments, the nanoparticles have an average diameter of from about 10 nm to about 160 nm after reconstitution. In some embodiments, the nanoparticles have an average diameter of from about 10 nm to about 150 nm after reconstitution. In some embodiments, the nanoparticles have an average diameter of from about 10 nm to about 140 nm after reconstitution. In some embodiments, the nanoparticles have an average diameter of from about 10 nm to about 130 nm after reconstitution. In some embodiments, the nanoparticles have an average diameter of from about 10 nm to about 120 nm after reconstitution. In some embodiments, the nanoparticles have an average diameter of from about 10 nm to about 110 nm after reconstitution. In some embodiments, the nanoparticles have an average diameter of from about 10 nm to about 100 nm after reconstitution. In some embodiments, the nanoparticles have an average diameter of from about 10 nm to about 90 nm after reconstitution. In some embodiments, the nanoparticles have an average diameter of from about 10 nm to about 80 nm after reconstitution. In some embodiments, the nanoparticles have an average diameter of from about 10 nm to about 70 nm after reconstitution. In some embodiments, the nanoparticles have an average diameter of from about 10 nm to about 60 nm after reconstitution. In some embodiments, the nanoparticles have an average diameter of from about 10 nm to about 50 nm after reconstitution. In some embodiments, the nanoparticles have an average diameter of from about 10 nm to about 40 nm after reconstitution. In some embodiments, the nanoparticles have an average diameter of from about 10 nm to about 30 nm after reconstitution. In some embodiments, the nanoparticles have an average diameter of from about 10 nm to about 20 nm after reconstitution.

In some embodiments, the nanoparticles have an average diameter of from about 20 nm to about 1000 nm after reconstitution. In some embodiments, the nanoparticles have an average diameter of from about 20 nm to about 950 nm after reconstitution. In some embodiments, the nanoparticles have an average diameter of from about 20 nm to about 900 nm after reconstitution. In some embodiments, the nanoparticles have an average diameter of from about 20 nm to about 850 nm after reconstitution. In some embodiments, the nanoparticles have an average diameter of from about 20 nm to about 800 nm after reconstitution. In some embodiments, the nanoparticles have an average diameter of from about 20 nm to about 750 nm after reconstitution. In some embodiments, the nanoparticles have an average diameter of from about 20 nm to about 700 nm after reconstitution. In some embodiments, the nanoparticles have an average diameter of from about 20 nm to about 650 nm after reconstitution. In some embodiments, the nanoparticles have an average diameter of from about 20 nm to about 600 nm after reconstitution. In some embodiments, the nanoparticles have an average diameter of from about 20 nm to about 550 nm after reconstitution. In some embodiments, the nanoparticles have an average diameter of from about 20 nm to about 500 nm after reconstitution. In some embodiments, the nanoparticles have an average diameter of from about 20 nm to about 450 nm after reconstitution. In some embodiments, the nanoparticles have an average diameter of from about 20 nm to about 400 nm after reconstitution. In some embodiments, the nanoparticles have an average diameter of from about 20 nm to about 350 nm after reconstitution. In some embodiments, the nanoparticles have an average diameter of from about 20 nm to about 300 nm after reconstitution. In some embodiments, the nanoparticles have an average diameter of from about 20 nm to about 250 nm after reconstitution. In some embodiments, the nanoparticles have an average diameter of from about 20 nm to about 240 nm after reconstitution. In some embodiments, the nanoparticles have an average diameter of from about 20 nm to about 230 nm after reconstitution. In some embodiments, the nanoparticles have an average diameter of from about 20 nm to about 220 nm after reconstitution. In some embodiments, the nanoparticles have an average diameter of from about 20 nm to about 210 nm after reconstitution. In some embodiments, the nanoparticles have an average diameter of from about 20 nm to about 200 nm after reconstitution. In some embodiments, the nanoparticles have an average diameter of from about 20 nm to about 190 nm after reconstitution. In some embodiments, the nanoparticles have an average diameter of from about 20 nm to about 180 nm after reconstitution. In some embodiments, the nanoparticles have an average diameter of from about 20 nm to about 170 nm after reconstitution. In some embodiments, the nanoparticles have an average diameter of from about 20 nm to about 160 nm after reconstitution. In some embodiments, the nanoparticles have an average diameter of from about 20 nm to about 150 nm after reconstitution. In some embodiments, the nanoparticles have an average diameter of from about 20 nm to about 140 nm after reconstitution. In some embodiments, the nanoparticles have an average diameter of from about 20 nm to about 130 nm after reconstitution. In some embodiments, the nanoparticles have an average diameter of from about 20 nm to about 120 nm after reconstitution. In some embodiments, the nanoparticles have an average diameter of from about 20 nm to about 110 nm after reconstitution. In some embodiments, the nanoparticles have an average diameter of from about 20 nm to about 100 nm after reconstitution. In some embodiments, the nanoparticles have an average diameter of from about 20 nm to about 90 nm after reconstitution. In some embodiments, the nanoparticles have an average diameter of from about 20 nm to about 80 nm after reconstitution. In some embodiments, the nanoparticles have an average diameter of from about 20 nm to about 70 nm after reconstitution. In some embodiments, the nanoparticles have an average diameter of from about 20 nm to about 60 nm after reconstitution. In some embodiments, the nanoparticles have an average diameter of from about 20 nm to about 50 nm after reconstitution. In some embodiments, the nanoparticles have an average diameter of from about 20 nm to about 40 nm after reconstitution. In some embodiments, the nanoparticles have an average diameter of from about 20 nm to about 30 nm after reconstitution.

In some embodiments, the nanoparticles have an average diameter of from about 30 nm to about 1000 nm after reconstitution. In some embodiments, the nanoparticles have an average diameter of from about 30 nm to about 950 nm after reconstitution. In some embodiments, the nanoparticles have an average diameter of from about 30 nm to about 900 nm after reconstitution. In some embodiments, the nanoparticles have an average diameter of from about 30 nm to about 850 nm after reconstitution. In some embodiments, the nanoparticles have an average diameter of from about 30 nm to about 800 nm after reconstitution. In some embodiments, the nanoparticles have an average diameter of from about 30 nm to about 750 nm after reconstitution. In some embodiments, the nanoparticles have an average diameter of from about 30 nm to about 700 nm after reconstitution. In some embodiments, the nanoparticles have an average diameter of from about 30 nm to about 650 nm after reconstitution. In some embodiments, the nanoparticles have an average diameter of from about 30 nm to about 600 nm after reconstitution. In some embodiments, the nanoparticles have an average diameter of from about 30 nm to about 550 nm after reconstitution. In some embodiments, the nanoparticles have an average diameter of from about 30 nm to about 500 nm. In some embodiments, the nanoparticles have an average diameter of from about 30 nm to about 450 nm after reconstitution. In some embodiments, the nanoparticles have an average diameter of from about 30 nm to about 400 nm after reconstitution. In some embodiments, the nanoparticles have an average diameter of from about 30 nm to about 350 nm after reconstitution. In some embodiments, the nanoparticles have an average diameter of from about 30 nm to about 300 nm after reconstitution. In some embodiments, the nanoparticles have an average diameter of from about 30 nm to about 250 nm after reconstitution. In some embodiments, the nanoparticles have an average diameter of from about 30 nm to about 240 nm after reconstitution. In some embodiments, the nanoparticles have an average diameter of from about 30 nm to about 230 nm after reconstitution. In some embodiments, the nanoparticles have an average diameter of from about 30 nm to about 220 nm after reconstitution. In some embodiments, the nanoparticles have an average diameter of from about 30 nm to about 210 nm after reconstitution. In some embodiments, the nanoparticles have an average diameter of from about 30 nm to about 200 nm after reconstitution. In some embodiments, the nanoparticles have an average diameter of from about 30 nm to about 190 nm after reconstitution. In some embodiments, the nanoparticles have an average diameter of from about 30 nm to about 180 nm after reconstitution. In some embodiments, the nanoparticles have an average diameter of from about 30 nm to about 170 nm after reconstitution. In some embodiments, the nanoparticles have an average diameter of from about 30 nm to about 160 nm after reconstitution. In some embodiments, the nanoparticles have an average diameter of from about 30 nm to about 150 nm after reconstitution. In some embodiments, the nanoparticles have an average diameter of from about 30 nm to about 140 nm after reconstitution. In some embodiments, the nanoparticles have an average diameter of from about 30 nm to about 130 nm after reconstitution. In some embodiments, the nanoparticles have an average diameter of from about 30 nm to about 120 nm after reconstitution. In some embodiments, the nanoparticles have an average diameter of from about 30 nm to about 110 nm after reconstitution. In some embodiments, the nanoparticles have an average diameter of from about 30 nm to about 100 nm after reconstitution. In some embodiments, the nanoparticles have an average diameter of from about 30 nm to about 90 nm after reconstitution. In some embodiments, the nanoparticles have an average diameter of from about 30 nm to about 80 nm after reconstitution. In some embodiments, the nanoparticles have an average diameter of from about 30 nm to about 70 nm after reconstitution. In some embodiments, the nanoparticles have an average diameter of from about 30 nm to about 60 nm after reconstitution. In some embodiments, the nanoparticles have an average diameter of from about 30 nm to about 50 nm after reconstitution. In some embodiments, the nanoparticles have an average diameter of from about 30 nm to about 40 nm after reconstitution.

In some embodiments, the nanoparticles have an average diameter of from about 40 nm to about 1000 nm after reconstitution. In some embodiments, the nanoparticles have an average diameter of from about 40 nm to about 950 nm after reconstitution. In some embodiments, the nanoparticles have an average diameter of from about 40 nm to about 900 nm after reconstitution. In some embodiments, the nanoparticles have an average diameter of from about 40 nm to about 850 nm after reconstitution. In some embodiments, the nanoparticles have an average diameter of from about 40 nm to about 800 nm after reconstitution. In some embodiments, the nanoparticles have an average diameter of from about 40 nm to about 750 nm after reconstitution. In some embodiments, the nanoparticles have an average diameter of from about 40 nm to about 700 nm after reconstitution. In some embodiments, the nanoparticles have an average diameter of from about 40 nm to about 650 nm after reconstitution. In some embodiments, the nanoparticles have an average diameter of from about 40 nm to about 600 nm after reconstitution. In some embodiments, the nanoparticles have an average diameter of from about 40 nm to about 550 nm after reconstitution. In some embodiments, the nanoparticles have an average diameter of from about 40 nm to about 500 nm after reconstitution. In some embodiments, the nanoparticles have an average diameter of from about 40 nm to about 450 nm after reconstitution. In some embodiments, the nanoparticles have an average diameter of from about 40 nm to about 400 nm after reconstitution. In some embodiments, the nanoparticles have an average diameter of from about 40 nm to about 350 nm after reconstitution. In some embodiments, the nanoparticles have an average diameter of from about 40 nm to about 300 nm. In some embodiments, the nanoparticles have an average diameter of from about 40 nm to about 250 nm after reconstitution. In some embodiments, the nanoparticles have an average diameter of from about 40 nm to about 240 nm after reconstitution. In some embodiments, the nanoparticles have an average diameter of from about 40 nm to about 230 nm after reconstitution. In some embodiments, the nanoparticles have an average diameter of from about 40 nm to about 220 nm after reconstitution. In some embodiments, the nanoparticles have an average diameter of from about 40 nm to about 210 nm after reconstitution. In some embodiments, the nanoparticles have an average diameter of from about 40 nm to about 200 nm after reconstitution. In some embodiments, the nanoparticles have an average diameter of from about 40 nm to about 190 nm after reconstitution. In some embodiments, the nanoparticles have an average diameter of from about 40 nm to about 180 nm after reconstitution. In some embodiments, the nanoparticles have an average diameter of from about 40 nm to about 170 nm after reconstitution. In some embodiments, the nanoparticles have an average diameter of from about 40 nm to about 160 nm after reconstitution. In some embodiments, the nanoparticles have an average diameter of from about 40 nm to about 150 nm after reconstitution. In some embodiments, the nanoparticles have an average diameter of from about 40 nm to about 140 nm after reconstitution. In some embodiments, the nanoparticles have an average diameter of from about 40 nm to about 130 nm after reconstitution. In some embodiments, the nanoparticles have an average diameter of from about 40 nm to about 120 nm after reconstitution. In some embodiments, the nanoparticles have an average diameter of from about 40 nm to about 110 nm after reconstitution. In some embodiments, the nanoparticles have an average diameter of from about 40 nm to about 100 nm after reconstitution. In some embodiments, the nanoparticles have an average diameter of from about 40 nm to about 90 nm after reconstitution. In some embodiments, the nanoparticles have an average diameter of from about 40 nm to about 80 nm after reconstitution. In some embodiments, the nanoparticles have an average diameter of from about 40 nm to about 70 nm after reconstitution. In some embodiments, the nanoparticles have an average diameter of from about 40 nm to about 60 nm after reconstitution. In some embodiments, the nanoparticles have an average diameter of from about 40 nm to about 50 nm after reconstitution.

In some embodiments, the nanoparticles have an average diameter of from about 50 nm to about 1000 nm after reconstitution. In some embodiments, the nanoparticles have an average diameter of from about 50 nm to about 950 nm after reconstitution. In some embodiments, the nanoparticles have an average diameter of from about 50 nm to about 900 nm after reconstitution. In some embodiments, the nanoparticles have an average diameter of from about 50 nm to about 850 nm after reconstitution. In some embodiments, the nanoparticles have an average diameter of from about 50 nm to about 800 nm after reconstitution. In some embodiments, the nanoparticles have an average diameter of from about 50 nm to about 750 nm after reconstitution. In some embodiments, the nanoparticles have an average diameter of from about 50 nm to about 700 nm after reconstitution. In some embodiments, the nanoparticles have an average diameter of from about 50 nm to about 650 nm after reconstitution. In some embodiments, the nanoparticles have an average diameter of from about 50 nm to about 600 nm after reconstitution. In some embodiments, the nanoparticles have an average diameter of from about 50 nm to about 550 nm after reconstitution. In some embodiments, the nanoparticles have an average diameter of from about 50 nm to about 500 nm after reconstitution. In some embodiments, the nanoparticles have an average diameter of from about 50 nm to about 450 nm after reconstitution. In some embodiments, the nanoparticles have an average diameter of from about 50 nm to about 400 nm after reconstitution. In some embodiments, the nanoparticles have an average diameter of from about 50 nm to about 350 nm after reconstitution. In some embodiments, the nanoparticles have an average diameter of from about 50 nm to about 300 nm after reconstitution. In some embodiments, the nanoparticles have an average diameter of from about 50 nm to about 250 nm after reconstitution. In some embodiments, the nanoparticles have an average diameter of from about 50 nm to about 240 nm after reconstitution. In some embodiments, the nanoparticles have an average diameter of from about 50 nm to about 230 nm after reconstitution. In some embodiments, the nanoparticles have an average diameter of from about 50 nm to about 220 nm after reconstitution. In some embodiments, the nanoparticles have an average diameter of from about 50 nm to about 210 nm after reconstitution. In some embodiments, the nanoparticles have an average diameter of from about 50 nm to about 200 nm after reconstitution. In some embodiments, the nanoparticles have an average diameter of from about 50 nm to about 190 nm after reconstitution. In some embodiments, the nanoparticles have an average diameter of from about 50 nm to about 180 nm after reconstitution. In some embodiments, the nanoparticles have an average diameter of from about 50 nm to about 170 nm after reconstitution. In some embodiments, the nanoparticles have an average diameter of from about 50 nm to about 160 nm after reconstitution. In some embodiments, the nanoparticles have an average diameter of from about 50 nm to about 150 nm after reconstitution. In some embodiments, the nanoparticles have an average diameter of from about 50 nm to about 140 nm after reconstitution. In some embodiments, the nanoparticles have an average diameter of from about 50 nm to about 130 nm after reconstitution. In some embodiments, the nanoparticles have an average diameter of from about 50 nm to about 120 nm after reconstitution. In some embodiments, the nanoparticles have an average diameter of from about 50 nm to about 110 nm after reconstitution. In some embodiments, the nanoparticles have an average diameter of from about 50 nm to about 100 nm after reconstitution. In some embodiments, the nanoparticles have an average diameter of from about 50 nm to about 90 nm after reconstitution. In some embodiments, the nanoparticles have an average diameter of from about 50 nm to about 80 nm after reconstitution. In some embodiments, the nanoparticles have an average diameter of from about 50 nm to about 70 nm after reconstitution. In some embodiments, the nanoparticles have an average diameter of from about 50 nm to about 60 nm after reconstitution. In some embodiments, the nanoparticles have an average diameter of about 10 nm after reconstitution. In some embodiments, the nanoparticles have an average diameter of about 20 nm after reconstitution. In some embodiments, the nanoparticles have an average diameter of about 30 nm after reconstitution. In some embodiments, the nanoparticles have an average diameter of about 40 nm after reconstitution. In some embodiments, the nanoparticles have an average diameter of about 50 nm after reconstitution. In some embodiments, the nanoparticles have an average diameter of about 60 nm after reconstitution. In some embodiments, the nanoparticles have an average diameter of about 70 nm after reconstitution. In some embodiments, the nanoparticles have an average diameter of about 80 nm after reconstitution. In some embodiments, the nanoparticles have an average diameter of about 90 nm after reconstitution. In some embodiments, the nanoparticles have an average diameter of about 100 nm after reconstitution. In some embodiments, the nanoparticles have an average diameter of about 110 nm after reconstitution. In some embodiments, the nanoparticles have an average diameter of about 120 nm after reconstitution. In some embodiments, the nanoparticles have an average diameter of about 130 nm after reconstitution. In some embodiments, the nanoparticles have an average diameter of about 140 nm after reconstitution. In some embodiments, the nanoparticles have an average diameter of about 150 nm after reconstitution. In some embodiments, the nanoparticles have an average diameter of about 160 nm after reconstitution. In some embodiments, the nanoparticles have an average diameter of about 170 nm after reconstitution. In some embodiments, the nanoparticles have an average diameter of about 180 nm. In some embodiments, the nanoparticles have an average diameter of about 190 nm after reconstitution. In some embodiments, the nanoparticles have an average diameter of about 200 nm after reconstitution. In some embodiments, the nanoparticles have an average diameter of about 210 nm after reconstitution. In some embodiments, the nanoparticles have an average diameter of about 220 nm after reconstitution. In some embodiments, the nanoparticles have an average diameter of about 230 nm after reconstitution. In some embodiments, the nanoparticles have an average diameter of about 240 nm after reconstitution. In some embodiments, the nanoparticles have an average diameter of about 250 nm after reconstitution. In some embodiments, the nanoparticles have an average diameter of about 300 nm after reconstitution. In some embodiments, the nanoparticles have an average diameter of about 350 nm after reconstitution. In some embodiments, the nanoparticles have an average diameter of about 400 nm after reconstitution. In some embodiments, the nanoparticles have an average diameter of about 450 nm after reconstitution. In some embodiments, the nanoparticles have an average diameter of about 500 nm after reconstitution. In some embodiments, the nanoparticles have an average diameter of about 550 nm after reconstitution. In some embodiments, the nanoparticles have an average diameter of about 600 nm after reconstitution. In some embodiments, the nanoparticles have an average diameter of about 650 nm after reconstitution. In some embodiments, the nanoparticles have an average diameter of about 700 nm after reconstitution. In some embodiments, the nanoparticles have an average diameter of about 750 nm after reconstitution. In some embodiments, the nanoparticles have an average diameter of about 800 nm. In some embodiments, the nanoparticles have an average diameter of about 850 nm after reconstitution. In some embodiments, the nanoparticles have an average diameter of about 900 nm after reconstitution. In some embodiments, the nanoparticles have an average diameter of about 950 nm after reconstitution. In some embodiments, the nanoparticles have an average diameter of about 1000 nm after reconstitution.

Preparation of Nanoparticles

Provided in another aspect is a process of preparing any one of the compositions comprising the nanoparticles described herein, comprising:
  a) dissolving Compound 1 in a volatile solvent to form a solution comprising a dissolved Compound 1;
  b) adding the solution comprising the dissolved Compound 1 to a pharmaceutically acceptable carrier in an aqueous solution to form an emulsion;
  c) subjecting the emulsion to homogenization to form a homogenized emulsion; and
  d) subjecting the homogenized emulsion to evaporation of the volatile solvent to form the any one of the compositions described herein.

In some embodiments, the adding the solution comprising the dissolved Compound 1 to a pharmaceutically acceptable carrier in an aqueous solution from step b) further comprises mixing to form an emulsion. In some embodiments, the mixing is performed with a homogenizer. In some embodiments, the volatile solvent is a chlorinated solvent, alcohol, ketone, ester, ether, acetonitrile, or any combination thereof. In some embodiments, volatile solvent is a chlorinated solvent. Examples of chlorinated solvents include, but are not limited to, chloroform, dichloromethane, and 1,2, dichloroethane. In some embodiments, volatile solvent is an alcohol. Examples of alcohols, include but are not limited to, methanol, ethanol, butanol (such as t-butyl and n-butyl alcohol), and propanol (such as iso-propyl alcohol). In some embodiments, volatile solvent is a ketone. An example of a ketone includes, but is not limited to, acetone. In some embodiments, volatile solvent is an ester. An example of an ester includes, but is not limited to ethyl acetate. In some embodiments, volatile solvent is an ether. In some embodiments, the volatile solvent is acetonitrile. In some embodiments, the volatile solvent is mixture of a chlorinated solvent with an alcohol.

In some embodiments, the volatile solvent is chloroform, ethanol, butanol, methanol, propanol, or a combination thereof. In some embodiments, volatile solvent is a mixture of chloroform and ethanol. In some embodiments, the volatile solvent is methanol. In some embodiments, the volatile solvent is a mixture of chloroform and methanol. In some embodiments, the volatile solvent is butanol, such as t-butanol or n-butanol. In some embodiments, the volatile solvent is a mixture of chloroform and butanol. In some embodiments, the volatile solvent is acetone. In some embodiments, the volatile solvent is acetonitrile. In some embodiments, the volatile solvent is dichloromethane. In some embodiments, the volatile solvent is 1,2 dichloroethane. In some embodiments the volatile solvent is ethyl acetate. In some embodiments, the volatile solvent is isopropyl alcohol. In some embodiments, the volatile solvent is chloroform. In some embodiments, the volatile solvent is ethanol. In some embodiments, the volatile solvent is a combination of ethanol and chloroform.

In some embodiments, the homogenization is high pressure homogenization. In some embodiments, the emulsion is cycled through high pressure homogenization for an appropriate amount of cycles. In some embodiments, the appropriate amount of cycles is from about 2 to about 10 cycles. In some embodiments, the appropriate amount of cycles is about 1, about 2, about 3, about 4, about 5, about 6, about 7, about 8, about 9, or about 10 cycles.

In some embodiments, the evaporation is accomplished with suitable equipment known for this purpose. Such suitable equipment include, but not limited to, rotary evaporators, falling film evaporators, wiped film evaporators, spray driers, and the like that can be operated in batch mode or in continuous operation. In some embodiments, the evaporation is accomplished with a rotary evaporator. In some embodiments, the evaporation is under reduced pressure.

Administration

In some embodiments, the composition is suitable for injection. In some embodiments, the composition is suitable for parenteral administration. Examples of parenteral administration include but are not limited to subcutaneous injections, intravenous, or intramuscular injections or infusion techniques. In some embodiments, the composition is suitable for intravenous administration.

In some embodiments, the composition is administered intraperitoneally, intraarterially, intrapulmonarily, orally, by inhalation, intravesicularly, intramuscularly, intratracheally, subcutaneously, intraocularly, intratumorally, intrathecally, or transdermally. In some embodiments, the composition is administered intravenously. In some embodiments, the composition is administered intraarterially. In some embodiments, the composition is administered intrapulmonarily. In some embodiments, the composition is administered orally. In some embodiments, the composition is administered by inhalation. In some embodiments, the composition is administered intravesicularly. In some embodiments, the composition is administered intramuscularly. In some embodiments, the composition is administered intratracheally. In some embodiments, the composition is administered subcutaneously. In some embodiments, the composition is administered intraocularly. In some embodiments, the composition is administered intrathecally. In some embodiments, the composition is administered transdermally.

Methods

Also provided herein in another aspect is a method of treating a disease in a subject in need thereof comprising administering any one of the compositions described herein.

In some embodiments, disease is cancer. Examples of cancers, include but not limited to solid tumors (e.g., tumors of the lung, breast, colon, prostate, bladder, rectum, brain or endometrium), hematological malignancies (e.g., leukemias, lymphomas, myelomas), carcinomas (e.g. bladder carcinoma, renal carcinoma, breast carcinoma, colorectal carcinoma), neuroblastoma, or melanoma. Non-limiting examples of these cancers include cutaneous T-cell lymphoma (CTCL), noncutaneous peripheral T-cell lymphoma, lymphoma associated with human T-cell lymphotrophic virus (HTLV), adult T-cell leukemia/lymphoma (ATLL), acute lymphocytic leukemia, acute nonlymphocytic leukemia, chronic lymphocytic leukemia, chronic myelogenous leukemia, Hodgkin's disease, non-Hodgkin's lymphoma, multiple myeloma, mesothelioma, childhood solid tumors such as brain neuroblastoma, retinoblastoma, Wilms' tumor, bone cancer and soft-tissue sarcomas, common solid tumors of adults such as head and neck cancers (e.g., oral, laryngeal and esophageal), genito urinary cancers (e.g., prostate, bladder, renal, uterine, ovarian, testicular, rectal and colon), lung cancer, breast cancer, pancreatic cancer, melanoma and other skin cancers, stomach cancer, brain cancer, liver cancer, adrenal cancer, kidney cancer, thyroid cancer, basal cell carcinoma, squamous cell carcinoma of both ulcerating and papillary type, metastatic skin carcinoma, medullary carcinoma, osteo sarcoma, Ewing's sarcoma, veticulum cell sarcoma, Kaposi's sarcoma, neuroblastoma and retinoblastoma. In some embodiments, the cancer is breast cancer, ovarian cancer, non-small cell lung cancer, pancreatic cancer, or bladder cancer.

In some embodiments, the disease is caused by an infection. In some embodiments, the infection is viral. Examples of viral infection include, but are not limited to, picornaviruses (poliovirus, coxsackievirus, hepatitis A virus, echovirus, human rhinovirus, cardioviruses (e.g. mengovirus and encephalomyocarditis virus) and foot-and-mouth disease virus); immunodeficiency virus (e.g., HIV-1, HIV-2 and related viruses including FIV-1 and SIV-1); hepatitis B virus (HBV); papillomavirus; Epstein-Barr virus (EBV); T-cell leukemia virus, e.g., HTLV-I, HTLV-II and related viruses, including bovine leukemia virus (BLV) and simian T-cell leukemia virus (STLV-I); hepatitis C virus (HCV); cytomegalovirus (CMV); influenza virus; herpes simplex virus (HSV). In some embodiments, the viral infection is human immunodeficiency virus (HIV), hepatitis B virus (HBV), hepatitis C virus. (HCV), Epstein-Barr virus (EBV), cytomegalovirus (CMV), or herpes simplex virus (HSV).

In some embodiments, Compound 1 is used an anticancer agent. In some embodiments, Compound 1 is used an antiviral agent.

Also disclosed herein is a method of delivering Compound 1 to a subject in need thereof comprising administering any one of the compositions described herein.

Disclosed compositions are administered to patients (animals and humans) in need of such treatment in dosages that will provide optimal pharmaceutical efficacy. It will be appreciated that the dose required for use in any particular application will vary from patient to patient, not only with the particular composition selected, but also with the route of administration, the nature of the condition being treated, the age and condition of the patient, concurrent medication or special diets then being followed by the patient, and other factors, with the appropriate dosage ultimately being at the discretion of the attendant physician. For treating diseases noted above, a contemplated composition disclosed herein is administered orally, subcutaneously, topically, parenterally, by inhalation spray, or rectally in dosage unit formulations containing conventional non-toxic pharmaceutically acceptable carriers, adjuvants and vehicles. Parenteral administration include subcutaneous injections, intravenous, or intramuscular injections or infusion techniques.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:

ACN acetonitrile
Bn benzyl
BOC or Boc tert-butyl carbamate
DCC N,N'-dicyclohexylcarbodiimide
DCM dichloromethane
DIPEA N,N-diisopropylethylamine
DMAP 4-(N,N-dimethylamino)pyridine
DMF dimethylformamide
DMA N,N-dimethylacetamide
DMSO dimethylsulfoxide
equiv equivalent(s)
EDCI 1-(3-dimethylaminopropyl)-3-ethylcarbodiimide
Et ethyl
EtOH ethanol
EtOAc ethyl acetate
HF hydrofluoric acid
HMDS bis(trimethylsilyl)amine
HPLC high performance liquid chromatography
Me methyl
MeOH methanol
MMTr 4-methoxytrityl
MMTrCl 4-methoxytrityl chloride
MS mass spectroscopy
NMM N-methylmorpholine
NMR nuclear magnetic resonance
TBHP tert-butyl hydroperoxide
TEA triethylamine
TFA trifluoroacetic acid
THF tetrahydrofuran
TLC thin layer chromatography
TBDMSCl tert-butyldimethylsilyl chloride
TMSCl trimethylsilyl chloride
TMSOTf trimethylsilyl trifluoromethanesulfonate Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: Synthesis of (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl stearate (Compound 1)

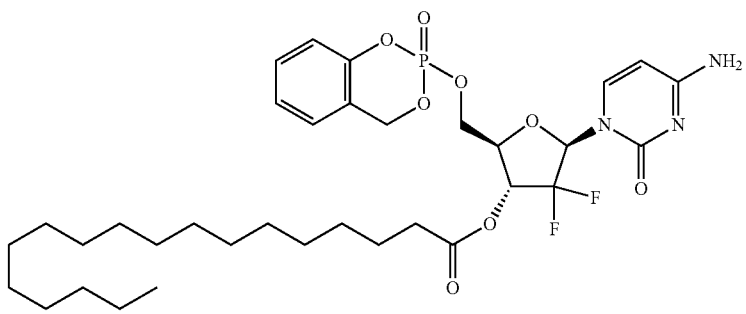

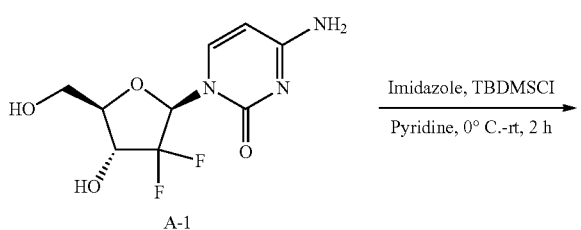

A-1

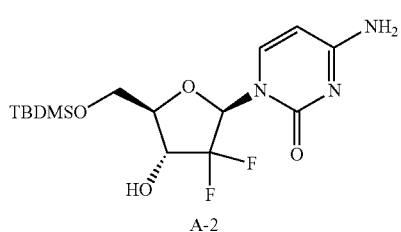
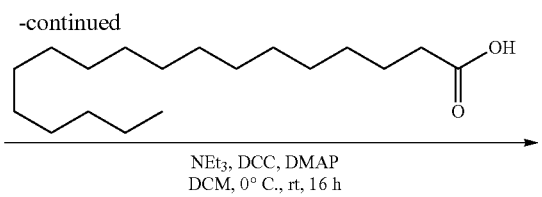
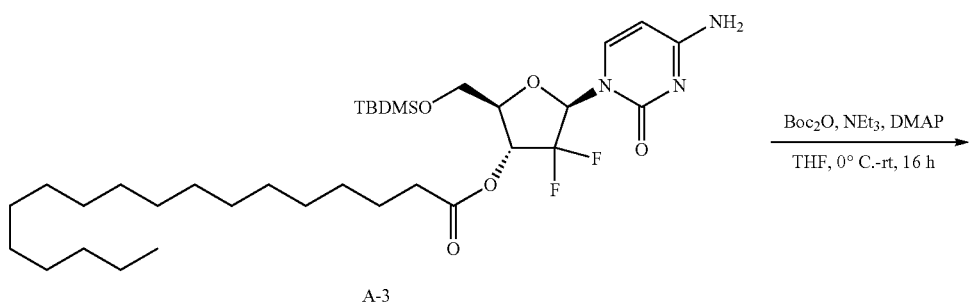
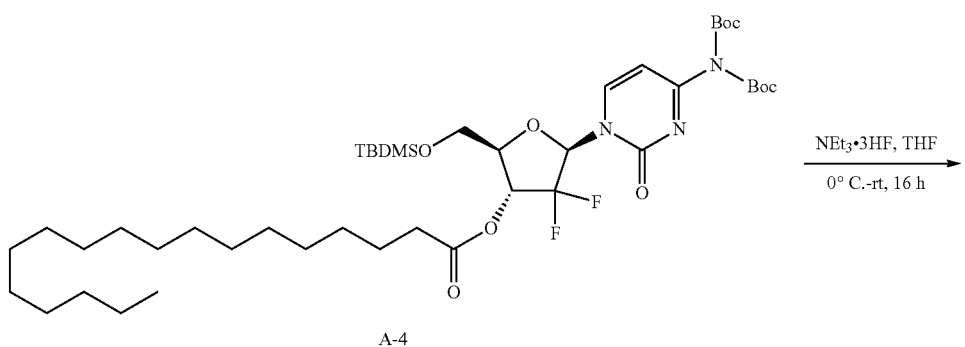
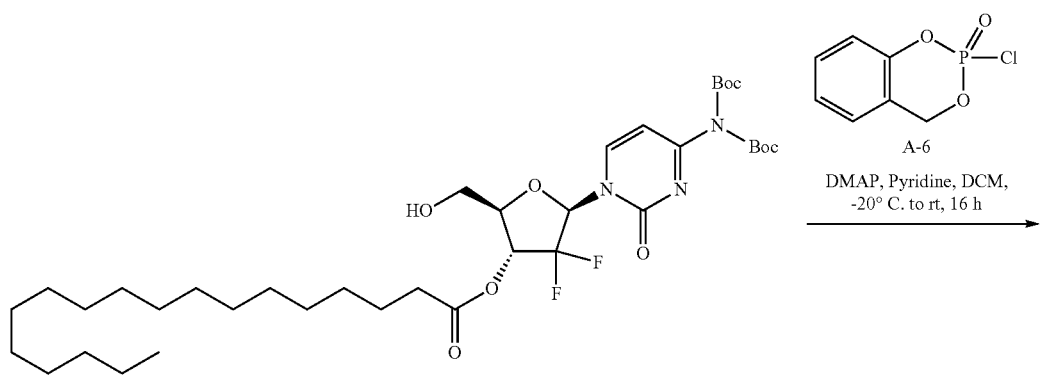
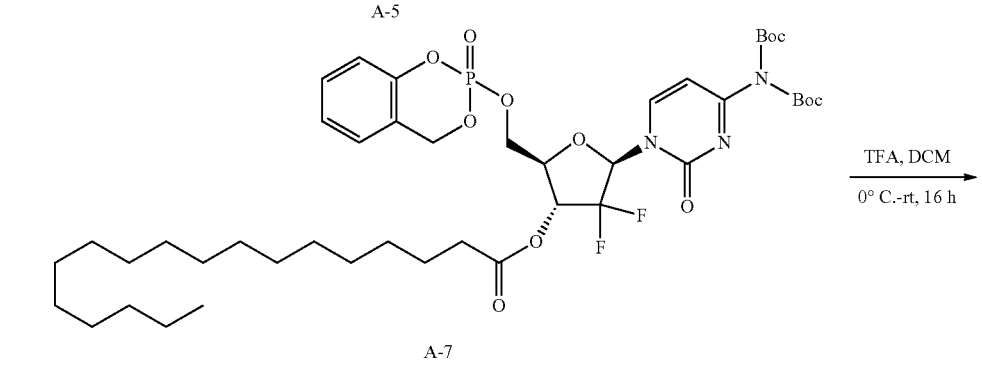

-continued

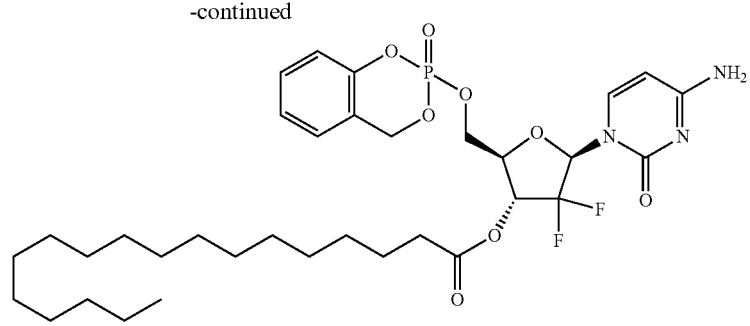

Compound 1

Synthesis of 2-chloro-4H-benzo[d][1,3,2]dioxaphosphinine 2-oxide (A-6)

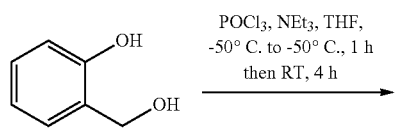

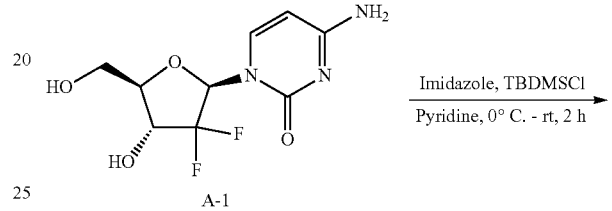

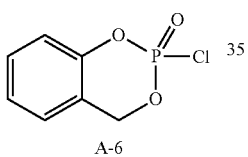

A-6

To a solution of freshly distilled POCl₃ (17 mL, 137 mmol) in dry THF (300 mL) was added a solution of 2-(hydroxymethyl)phenol (20 g, 161.29 mmol), Et₃N (49 mL, 2.4 vol) in dry THF (150 mL), over a period of 2 h, at −50° C. The reaction mixture was stirred at −50° C. for 1 h and slowly raised the temperature to rt and stirred for 4 h at rt. The reaction mixture was filtered under inert atmosphere and the filtrate was concentrated under reduced pressure. The crude material was purified by column chromatography (SiO₂, 100-200 mesh) to afford 2-chloro-4H-benzo[d][1,3,2]dioxaphosphinine 2-oxide A-6 (10 g, yield 30%) as a pale yellow liquid.

To a stirred solution of 4-amino-1-((2R,4R,5R)-3,3-difluoro-4-hydroxy-5-(hydroxymethyl)tetrahydrofuran-2-yl)pyrimidin-2(1H)-one A-1 (25 g, 94.98 mmol) in pyridine (250 mL, 10 vol.) at 0° C. was added imidazole (19.4 g, 284.95 mmol), TBDMS-Cl (21.5 g, 142.17 mmol) and stirred at rt for 2 h. Solvent was evaporated from the reaction mixture and residue was taken in water (300 mL) and extracted with EtOAc (4×200 mL). The combined organic layer was washed with water (300 mL), brine (300 mL), dried over Na₂SO₄, filtered and evaporated. The crude compound was purified by column chromatography (SiO₂, 100-200 mesh) to afford 4-amino-1-((2R,4R,5R)-5-(((tert-butyldimethylsilyl)oxy)methyl)-3,3-difluoro-4-hydroxytetrahydrofuran-2-yl)pyrimidin-2(1H)-one A-2 (17 g, 47%) as a white solid.

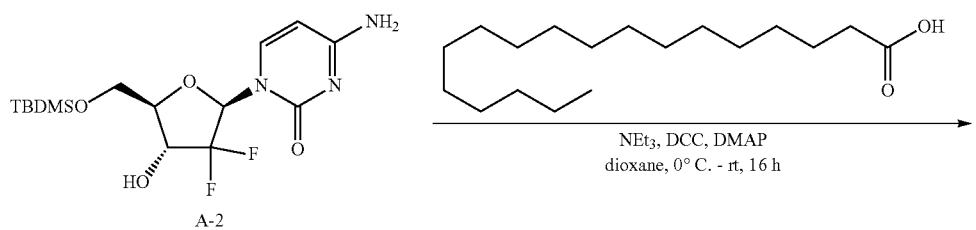

-continued

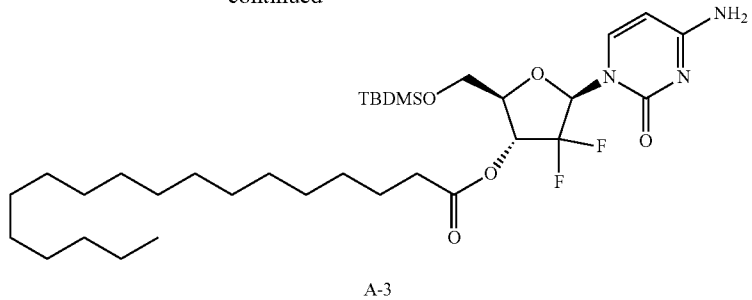

A-3

To a stirred solution of 4-amino-1-(((2R,4R,5R)-5-(((tert-butyldimethylsilyl)oxy)methyl)-3,3-difluoro-4-hydroxytetrahydrofuran-2-yl)pyrimidin-2(1H)-one A-2 (5.0 g, 13.2 mmol) in 1,4-dioxane (100 mL, 20 vol.) was added stearic acid (15 g, 52.98 mmol), Et$_3$N (9.3 mL, 66.23 mmol), DCC (13.6 g, 66.23 mmol) and DMAP (0.16 g, 1.3 mmol) at 0° C. and stirred at rt for 16 h. The reaction mixture was filtered through a pad of celite and celite bed was washed with EtOAc (2×50 mL). All the filtrates were combined and added water (200 mL) and extracted with EtOAc (2×100 mL). Organic layer was separated, given water wash (mL), dried over Na$_2$SO$_4$, filtered, and concentrated under reduced pressure. The crude material was purified by column chromatography (SiO$_2$, 100-200 mesh) to afford (2R,3R,5R)-5-(4-amino-2-oxopyrimidin-1(2H)-yl)-2-(((tert-butyldimethylsilyl)oxy)methyl)-4,4-difluorotetrahydrofuran-3-yl stearate A-3 (4.9 g, 57%) as a white solid.

To a stirred solution of (2R,3R,5R)-5-(4-amino-2-oxopyrimidin-1(2H)-yl)-2-(((tert-butyldimethylsilyl)oxy)methyl)-4,4-difluorotetrahydrofuran-3-yl stearate A-3 (9.8 g, 15.217 mmol) in THF (100 mL) was added NEt$_3$ (10.7 mL, 76.08 mmol) and DMAP (0.18 g, 1.52 mmol) followed by (Boc)$_2$O (8.04 mL, 34.99 mmol) at 0° C. The reaction mixture was stirred at rt for 16 h. The reaction mixture was diluted with water (300 mL) and extracted with ethyl acetate (3×150 mL). The combined organic layer was washed with brine (200 mL), dried over Na$_2$SO$_4$, filtered, and concentrated under reduced pressure. The crude compound was purified by column chromatography (SiO$_2$, 100-200 mesh) to afford (2R,3R,5R)-5-(4-((di-tert-butoxycarbonyl)amino)-2-oxopyrimidin-1(2H)-yl)-2-(((tert-butyldimethylsilyl)oxy)methyl)-4,4-difluorotetrahydrofuran-3-yl stearate A-4 (9 g, 70%) as a brown liquid.

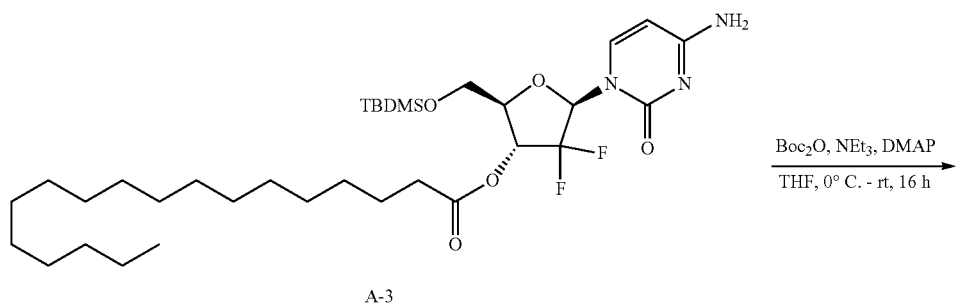

A-3

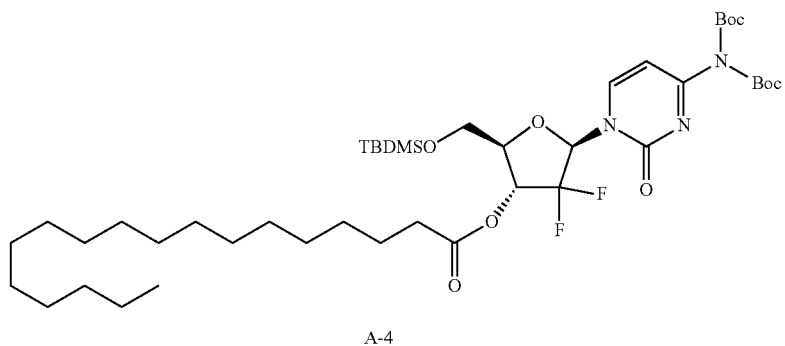

A-4

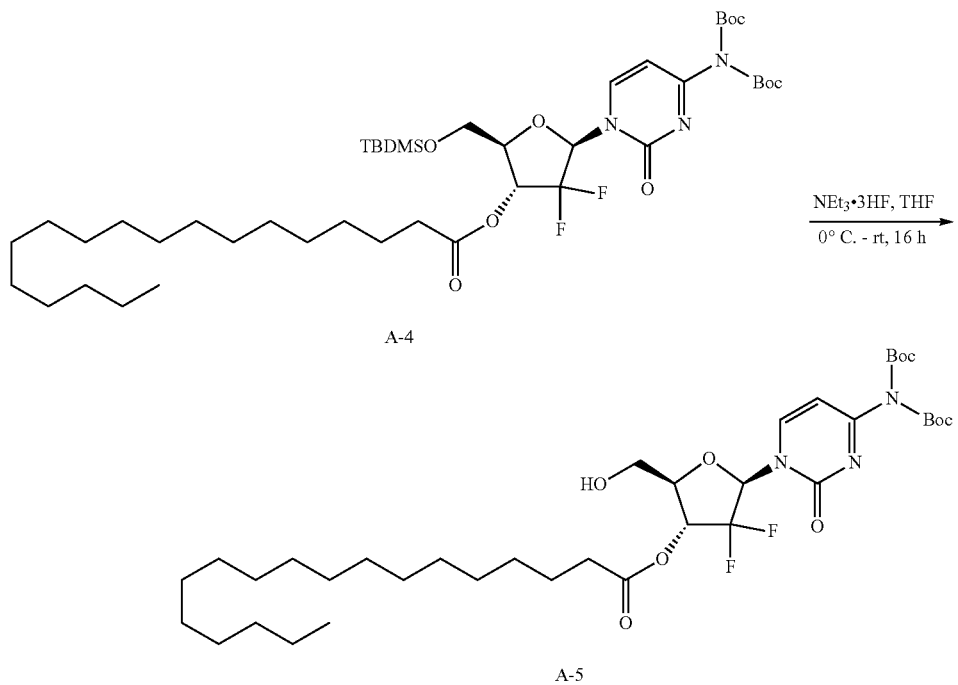

To a stirred solution of (2R,3R,5R)-5-(4-((di-tert-butoxycarbonyl)amino)-2-oxopyrimidin-1(2H)-yl)-2-(((tert-butyldimethylsilyl)oxy)methyl)-4,4-difluorotetrahydrofuran-3-yl stearate A-4 (9 g, 10.66 mmol) in THF (90 mL) was added NEt$_3$·0.3HF (8.7 mL, 54.03 mmol) dropwise over a period of 10 min at 0° C. The reaction mixture was slowly warm to room temperature and stirred for 16 h. The reaction mixture was diluted with water (150 mL) and extracted with ethyl acetate (3×100 mL). The combined organic layer was washed with brine (150 mL), dried over Na$_2$SO$_4$, filtered, and concentrated under reduced pressure. The crude compound was purified by column chromatography (SiO$_2$, 100-200 mesh) to afford (2R,3R,5R)-5-(4-((di-tert-butoxycarbonyl)amino)-2-oxopyrimidin-1(2H)-yl)-4,4-difluoro-2-(hydroxymethyl) tetrahydrofuran-3-yl stearate A-5 (5.2 g, 67%) as a yellow gummy liquid.

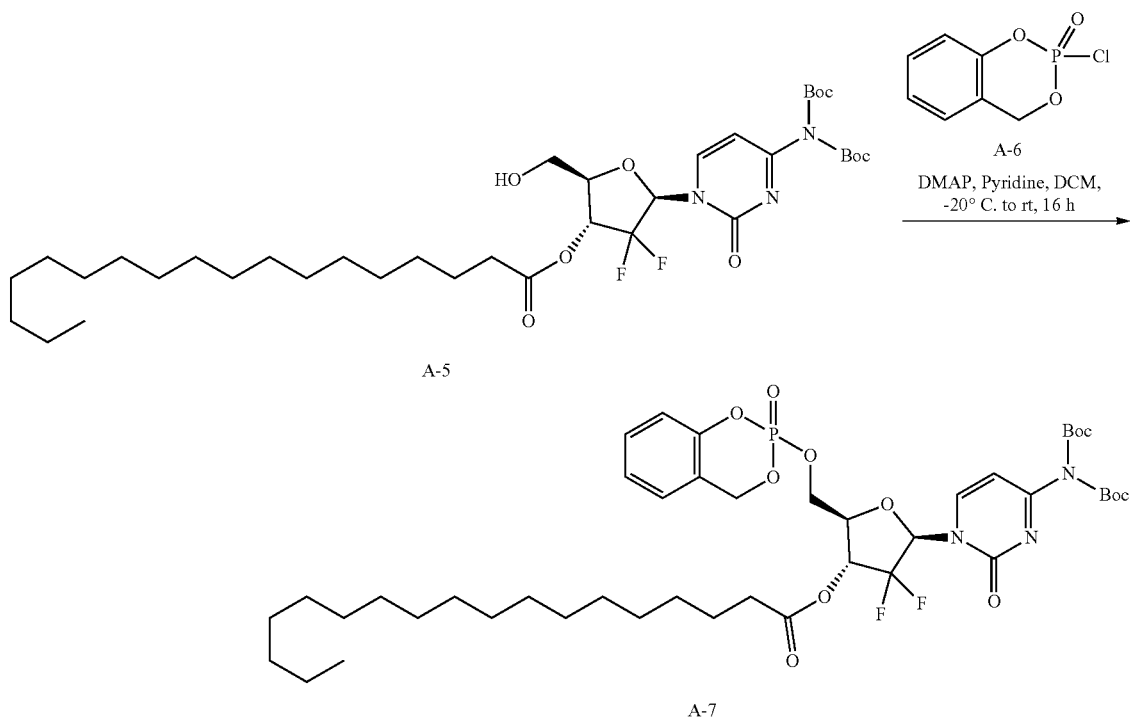

To a stirred solution of (2R,3R,5R)-5-(4-((di-tert-butoxycarbonyl)amino)-2-oxopyrimidin-1(2H)-yl)-4,4-difluoro-2-(hydroxymethyl) tetrahydrofuran-3-yl stearate A-5 (1 g, 1.37 mmol) in dry DCM (5 mL) and dry pyridine (5 mL) was added DMAP (84 mg, 0.685 mmol). To this mixture was added a solution of 2-chloro-4H-benzo[d][1,3,2]dioxaphosphinine 2-oxide A-6 (2.8 g, 13.7 mmol) in dry DCM (5 mL) dropwise over a period of 10 min at −20° C. The reaction mixture was slowly warmed to room temperature and stirred for 16 h. The reaction mixture was concentrated under reduced pressure and the residue was dissolved in 10% MeOH-DCM (50 mL), washed with water (2×50 mL), brine (25 mL), dried over Na$_2$SO$_4$, filtered, and evaporated under reduced pressure. The crude compound was purified by column chromatography (SiO$_2$, 100-200 mesh) to afford (2R,3R,5R)-5-(4-((di-tert-butoxycarbonyl)amino)-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl stearate A-7 (580 mg, 47%) as a pale yellow liquid.

5.53 (d, 1H), 5.49-5.37 (m, 3H), 4.51-4.37 (m, 3H), 2.39 (q, J=7.2 Hz, 2H), 1.52 (t, J=6.4 Hz, 2H), 1.23 (s, 28H), 0.85 (t, J=7.2 Hz, 3H).

Exemplary Nanoparticle Compositions Containing Gemcitabine Prodrug (Compound 1)

Example 2

49 mL of a human albumin solution (1.47% w/v) was prepared diluting from a 25% human albumin U.S.P. solution using chloroform saturated water. Compound 1 (60 mg) was dissolved in 1000 µL chloroform/ethanol (90:10 ratio). The organic solvent solution was added dropwise to the albumin solution while homogenizing for 5 minutes at 5000 rpm (IKA Ultra-Turrax T 18 rotor-stator, S 18N-19G dispersing element) to form a rough emulsion. This rough emulsion was transferred into a high-pressure homogenizer (Avestin, Emulsiflex-C5), where emulsification was performed by recycling the emulsion for 2.5 minutes at high

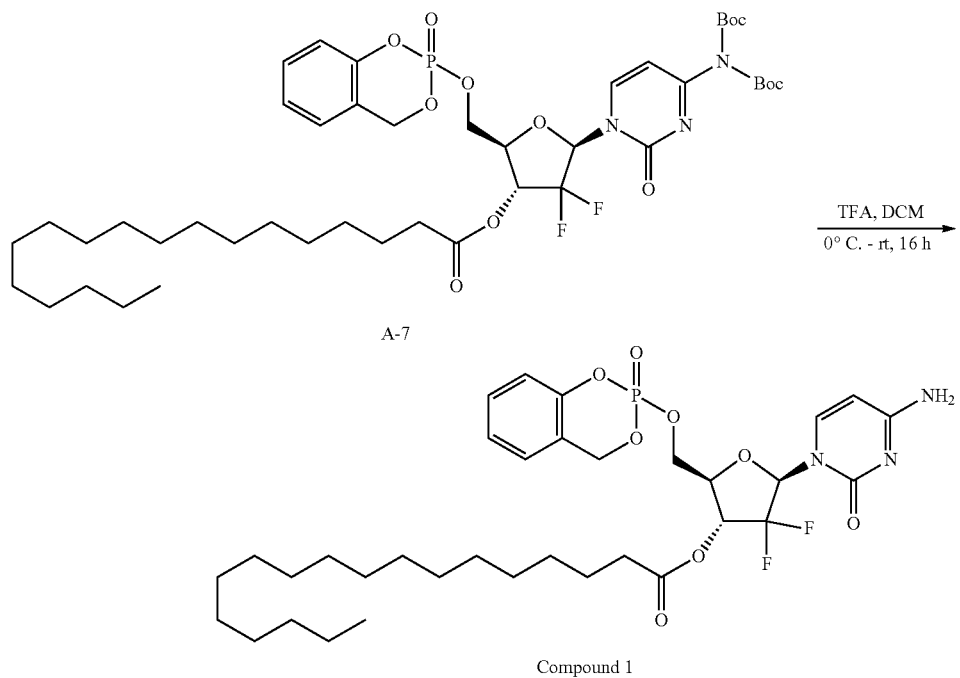

pressure (12,000 psi to 20,000 psi) while cooling (4° to 8° C.). The resulting emulsion was transferred into a rotary evaporator (Buchi, Switzerland), where the volatile solvents were removed at 40° C. under reduced pressure (approximately 25 mm Hg) for 8 minutes. The suspension was then filtered at 0.2 µm to yield approximately a 45 mL suspension. The entire preceding process was immediately repeated though removal of the volatile solvents in a second batch, and then both batches were combined and filtered at 0.2 µm to yield approximately a 90 mL combined suspension. The average particle size ($Z_{av}$, Malvern Nano-S) was determined to be 52 nm initially, 52 nm after 15 minutes, 52 nm after 30 minutes, 53 nm after 70 minutes, 54 nm after 120 minutes, and 73 nm after 29 hours at room temperature.

To a stirred solution of (2R,3R,5R)-5-(4-((di-tert-butoxycarbonyl)amino)-2-oxopyrimidin-1(2H)-yl)-4,4-difluoro-2-(((2-oxido-4H-benzo[d][1,3,2]dioxaphosphinin-2-yl)oxy)methyl)tetrahydrofuran-3-yl stearate A-7 (1.1 g, 1.22 mmol) in dry DCM (10 mL) at 0° C. was added TFA (0.95 mL, 12.2 mmol) dropwise. The reaction mixture was stirred at room temperature for 7 h. The solvent was evaporated and the residue was dissolved in 10% MeOH:DCM (100 mL) and washed with saturated NaHCO$_3$ (2×25 mL), dried over Na$_2$SO$_4$, filtered, and evaporated under reduced pressure. The crude compound was purified by column chromatography (SiO$_2$, 100-200 mesh) to afford (2R,3R,5R)-5-(4-amino-2-oxopyrimidin-1(2H)-yl)-4,4-difluoro-2-(((2-oxido-4H-benzo[d][1,3,2]dioxaphosphinin-2-yl)oxy)methyl) tetrahydrofuran-3-yl stearate (Compound 1) (0.54 g, 63%) as an off-white solid. MS(ESI) m/z 698.5 [M+H]$^+$; $^1$H NMR (400 MHz, DMSO-d$_6$) δ 7.47-7.35 (m, 4H), 7.3-7.28 (d, 1H), 7.23-7.19 (m, 1H), 7.14-7.11 (d, 1H), 6.22 (br s, 1H), Example 3

This example demonstrates the lyophilization and rehydration into each of: water, 5% dextrose water, 0.9% saline, and phosphate-buffered saline pH 7.4 (PBS) for a nanoparticle pharmaceutical composition comprising Compound 1 and albumin. Immediately after final 0.2 μm filtration, the nanoparticle suspension from Example 2 was flash frozen by immersing sample vials into liquid nitrogen followed by complete lyophilization overnight to yield a dry cake, and thereafter stored at −20° C. The cake was later reconstituted. Upon hydration into water, the average particle size ($Z_{av}$, Malvern Nano-S) was determined to be 64 nm initially, 62 nm after 60 minutes, 62 nm after 150 minutes, and 61 nm after 25 hours at room temperature. Upon hydration into 5% dextrose water, the average particle size ($Z_{av}$, Malvern Nano-S) was determined to be 75 nm initially, 74 nm after 60 minutes, 75 nm after 150 minutes, and 74 nm after 25 hours at room temperature. Upon hydration into 0.9% saline, the average particle size ($Z_{av}$, Malvern Nano-S) was determined to be 77 nm initially, 87 nm after 60 minutes, 91 nm after 150 minutes, and 107 nm after 25 hours at room temperature. Upon hydration into phosphate-buffered saline, the average particle size ($Z_{av}$, Malvern Nano-S) was determined to be 66 nm initially, 80 nm after 60 minutes, and 84 nm after 150 minutes.

Example 4

60 mL of a human albumin solution (1.44% w/v) was prepared diluting from a 25% human albumin U.S.P. solution using chloroform saturated water. Compound 1 (63 mg) was dissolved in 1200 μL chloroform/ethanol (90:10 ratio). The organic solvent solution was added dropwise to the albumin solution while homogenizing for 5 minutes at 5000 rpm (IKA Ultra-Turrax T 18 rotor-stator, S 18N-19G dispersing element) to form a rough emulsion. This rough emulsion was transferred into a high-pressure homogenizer (Microfluidics, LM20 Microfluidizer with an 87 μm G10Z interaction chamber), where emulsification was performed by recycling the emulsion for 5 minutes after first pass at 10,000 psi while cooling (1° to 4° C.). The resulting emulsion was transferred into a rotary evaporator (Buchi, Switzerland), where the volatile solvents were removed at 40° C. under reduced pressure (approximately 25 mm Hg) for 7 minutes. The suspension was then filtered at 0.2 μm to yield an approximate 52 mL suspension. The average particle size (Zav, Malvern Nano-S) was determined to be 44 nm initially, 44 nm after 15 minutes, 44 nm after 30 minutes, 44 nm after 60 minutes, 46 nm after 120 minutes, and 67 nm after 25 hours at room temperature.

Example 5

This example demonstrates the lyophilization and rehydration into each of: water, 5% dextrose water, 0.9% saline, and phosphate-buffered saline pH 7.4 (PBS) for a nanoparticle pharmaceutical composition comprising Compound 1 and albumin. Immediately after final 0.2 μm filtration, the nanoparticle suspension from Example 4 was flash frozen by immersing sample vials into liquid nitrogen followed by complete lyophilization overnight to yield a dry cake, and thereafter stored at −20° C. The cake was later reconstituted. Upon hydration into water, the average particle size (Zav, Malvern Nano-S) was determined to be 49 nm initially, 48 nm after 60 minutes, and 48 nm after 140 minutes at room temperature. Upon hydration into 0.9% saline, the average particle size (Zav, Malvern Nano-S) was determined to be 50 nm initially, 56 nm after 60 minutes, and 58 nm after 140 minutes at room temperature. Upon hydration into phosphate-buffered saline, the average particle size (Zav, Malvern Nano-S) was determined to be 49 nm initially, 55 nm after 60 minutes, and 56 nm after 140 minutes at room temperature. Upon hydration into 5% dextrose water, the average particle size (Zav, Malvern Nano-S) was determined to be 55 nm initially, 54 nm after 60 minutes, and 53 nm after 140 minutes at room temperature.

Example 6: In vivo Xenograft Efficacy (Human Ovarian Tumor)

This example demonstrates the efficacy of nanoparticles of Compound 1 and albumin in vivo. A nanoparticle composition comprising Compound 1 and albumin from Example 2 was tested in an in vivo xenograft efficacy model in tumor-bearing mice. Athymic Nude-Foxn1nu mice were implanted subcutaneously with a human patient-derived xenograft (PDX) derived from a human ovarian tumor (CTG-1180, Champions Oncology). Tumors were allowed grow to ~200 cubic mm before commencement of treatment (day 0). Lyophilized nanoparticle formulations of Compound 1 were rehydrated in 5% dextrose in sterile water (D5W) immediately prior to dosing. Mice were then dosed intravenously with various concentrations of gemcitabine, nanoparticle formulation of Compound 1, or vehicle control (dissolved directly in D5W and dosed in mg of gemcitabine/compound 1 per kg of mouse body weight abbreviated as mpk) once weekly for 4 weeks (mice were dosed on day 0, 7, 14, and 21 with no treatments thereafter). Dosing was done in 5 mice per arm: Arm 1-D5W vehicle control, Arm 2-Gemcitabine 40 mpk (152 μmol/kg), Arm 3-Gemcitabine 100 mpk (380 μmol/kg), Arm 4-Compound 1 albumin nanoparticle 25 mpk (36 μmol/kg), and Arm 5-Compound 1 albumin nanoparticle 50 mpk (72 μmol/kg). The vehicle control arm was sacrificed after day 28 when tumors became too large. Tumor volume was assessed by caliper measurement using the following formula: Tumor volume=width$^2$×length×0.52. Tumor growth inhibition (TGI) at day 28 was assessed using the following formula: %TGI=100×([Volume at day 28-Volume at day 0] for treatment group)/([Volume at day 28-Volume at day 0] for vehicle control group). As shown in The Figure, TGI was 88% for gemcitabine 40 mpk, 98% for gemcitabine 100 mpk, 92% for Compound 1 albumin nanoparticle 25 mpk, and 106% for Compound 1 albumin nanoparticle 50 mpk. Treated arms continued to be observed through day 46 for tumor regrowth, without additional treatment beyond day 21. Compound 1 albumin nanoparticle arms showed less or no tumor regrowth at lower doses (on a mpk basis) as compared to gemcitabine arms. This finding was even more pronounced when the arms were compared on a molar basis (μmol drug/kg).

Example 7: In Vivo Xenograft Efficacy (Human Pancreatic Adenocarcinoma Tumor)

Athymic Nude-Foxn1nu mice are implanted subcutaneously with a human patient-derived xenograft (PDX) derived from a human pancreatic adenocarcinoma tumor (CTG-0687, Champions Oncology). Tumors are allowed grow to ~200 cubic mm before commencement of treatment (day 0). Lyophilized nanoparticle formulations of Compound 1 are rehydrated in sterile 0.9% NaCl in water immediately prior to dosing. Mice are then dosed intravenously with various nanoparticle formulations of Compound 1 (dissolved directly in 0.9% NaCl) twice weekly for 4 weeks. Tumor volume is assessed by caliper measurement using the following formula: Tumor volume=width$^2$×length×0.52. Tumor growth inhibition (TGI) at day 25 is assessed using the following formula: % TGI=100×([Volume at day 25−Volume at day 0] for treatment group)/([Volume at day 25−Volume at day 0] for vehicle control group).

Example 8: Cellular Pharmacology

Compound 1 is tested for its ability to impair cancer cell proliferation and/or induce cell death. For cellular proliferation studies, cultured cells are treated with the test compound for 24-120 hours. After compound treatment, cell proliferation is assessed by using methods including, but not limited to, Cell-Titer-Glo® (Promega), Alamar Blue, LIVE/DEAD® (ThermoFisher), BrdU incorporation, and live-cell imaging. The cancer lines used include, but are not limited to BxPC-3 (pancreatic cancer). Gemcitabine hydrochloride serves as a control for activity.

Example 8A: Cellular Proliferation Assay in BxPC-3 Cells

BxPC-3 (pancreatic adenocarcinoma) cell line is purchased from the American Type Culture Collection (Catalog # CRL-1687) and grows in RPMI-1640 medium (e.g. Corning #10-040-CV) with 10% Heat Inactivated Fetal Calf Serum at 37° C. and 5% CO2 (as recommended by the ATCC).

Cultures are grown in 175 mm$^2$ plates to 80% confluence, and cells are trypsinized to a single-cell suspension. Cells are then resuspended in growth medium to a density of 25,00 cells/ml. They are then plated into 96-well assay plates (Corning #3917) in a volume of 100 ul/well (2,500 cells/well). Cells are allowed to adhere to plates for 24 h at 37° C. and 5% $CO_2$). Compound 1 is then added to the wells using an 11-fold serial dilution scheme (over 9 dilutions, generally ranging from 30 μM-30 pM), and the cells are incubated for an additional 120 hours. After 120 h, 90 ul of Cell-Titer Glo reagent (Promega #G7572) is added, and the plates are read using a luminescence counter (e.g., BioTek Synergy HTX at 100 ms read time).

Potency determination are performed by 4-parameter fit of the dose vs. luminescence data using XLFit software (IDBS) with a one site dose response model (Model 205; fit=(A+((B−A)/(1+((C/x)^D)))). The $EC_{50}$ is generally expressed as the inflection point (C parameter) for the fit when the upper and lower portions of the response curve were well-defined. In cases where full inhibition of cell growth was not observed at the highest concentration used, $EC_{50}$ is reported as the concentration that resulted in 50% loss of Cell-Titer-Glo signal (compared to untreated control).

What is claimed is:

1. A compound that is:

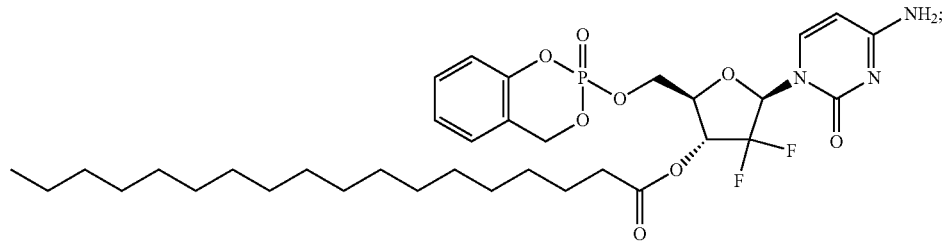 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

or a pharmaceutically acceptable salt thereof.

2. A pharmaceutical composition comprising a compound of claim 1, or a pharmaceutically acceptable salt thereof, and at least one pharmaceutically acceptable excipient.

3. A composition comprising nanoparticles, wherein the nanoparticles comprise a pharmaceutically acceptable carrier comprising albumin and a compound that is:

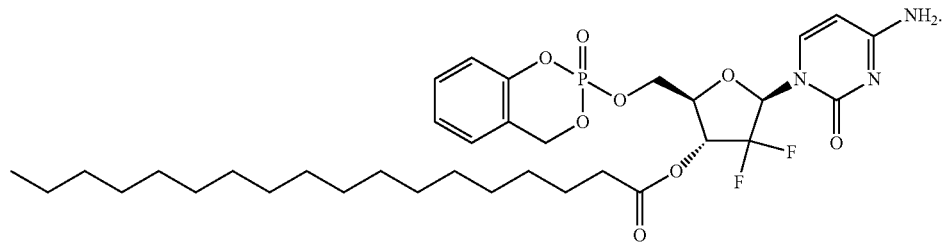 [SMILES: CCCCCCCCCCCCCCCCCC(=O)O[C@@H]1[C@@H](COP2(=O)OCc3ccccc3O2)O[C@@H](n2ccc(N)nc2=O)C1(F)F]

4. The composition of claim 3, wherein the nanoparticles have an average diameter of from about 10 nm to about 1000 nm.

5. The composition of claim 4, wherein the nanoparticles have an average diameter of from about 30 nm to about 250 nm.

6. The composition of claim 3, wherein the albumin is human serum albumin.

7. The composition of claim 3, wherein the molar ratio of the compound to pharmaceutically acceptable carrier is from about 1:1 to about 20:1.

8. The composition of claim 7, wherein the molar ratio of the compound to pharmaceutically acceptable carrier is from about 2:1 to about 12:1.

9. The composition of claim 3, wherein the composition is dehydrated.

10. The composition of claim 9, wherein the composition is a lyophilized composition.

11. The composition of claim 10, wherein the composition comprises from about 0.9% to about 24% by weight of the compound.

12. The composition of claim 10, wherein the composition comprises from about 76% to about 99% by weight of the pharmaceutically acceptable carrier.

13. The composition of claim 12, wherein the composition comprises from about 84% to about 98% by weight of the pharmaceutically acceptable carrier.

14. The composition of claim 10, wherein the composition is reconstituted with a biocompatible liquid to provide a reconstituted composition.

15. The composition of claim 14, wherein the biocompatible liquid is a buffered solution, a solution comprising dextrose, or a solution comprising one or more salts.

16. The composition of claim 14, wherein the biocompatible liquid is sterile water, saline, phosphate-buffered saline, 5% dextrose in water solution, Ringer's solution, or Ringer's lactate solution.

17. The composition of claim 14, wherein the nanoparticles have an average diameter of from about 10 nm to about 1000 nm after reconstitution.

18. The composition of claim 17, wherein the nanoparticles have an average diameter of from about 30 nm to about 250 nm after reconstitution.

* * * * *